United States Patent
Mao et al.

(10) Patent No.: US 10,393,736 B2
(45) Date of Patent: Aug. 27, 2019

(54) ANTI-FOULING SALINE AND SILOXANE COATED PARTICLES, SUBSTRATES, POLYMERS AND USES RELATED THERETO

(71) Applicants: Emory University, Atlanta, GA (US); Children's Healthcare of Atlanta, Inc., Atlanta, GA (US)

(72) Inventors: Hui Mao, Johns Creek, GA (US); Yuancheng Li, Atlanta, GA (US); Lily Yang, Atlanta, GA (US)

(73) Assignees: Emory University, Atlanta, GA (US); Children's Healthcare of Atlanta, Inc., Atlanta, GA (US)

( * ) Notice: Subject to any disclaimer, the term of this patent is extended or adjusted under 35 U.S.C. 154(b) by 0 days.

(21) Appl. No.: 15/476,722

(22) Filed: Mar. 31, 2017

(65) Prior Publication Data
US 2017/0285020 A1 Oct. 5, 2017

Related U.S. Application Data

(60) Provisional application No. 62/317,239, filed on Apr. 1, 2016.

(51) Int. Cl.
*C08G 65/336* (2006.01)
*G01N 33/543* (2006.01)
(Continued)

(52) U.S. Cl.
CPC ....... *G01N 33/54346* (2013.01); *C08G 77/46* (2013.01); *C12N 13/00* (2013.01);
(Continued)

(58) Field of Classification Search
CPC ...... C09C 1/3081; C08G 65/336; C07F 7/081
See application file for complete search history.

(56) References Cited

U.S. PATENT DOCUMENTS 2,946,701 A * 7/1960 Plueddemann ......... C03C 25/40
166/295
4,352,917 A * 10/1982 Tripp ................... C08G 65/336
427/387
(Continued)

FOREIGN PATENT DOCUMENTS

WO 1999062079 12/1999
WO 20090280063 11/2009
(Continued)

OTHER PUBLICATIONS

Anbarasu et al. Synthesis and characterization of polyethylene glycol (PEG) coated Fe3O4 nanoparticles by chemical co-precipitation method for biomedical applications, Spectrochimica Acta Part A: Molecular and Biomolecular Spectroscopy 135 (2015) 536-539.
(Continued)

*Primary Examiner* — Margaret G Moore
(74) *Attorney, Agent, or Firm* — Emory Patent Group

(57) ABSTRACT

This disclosure relates to polymer coatings with desirable anti-fouling properties. In certain embodiments, polymers are coated on particles which allow for conjugation with targeting moieties. In certain embodiments, the particles are nanoparticles with targeting moieties that bind with tumor associated antigens.

12 Claims, 9 Drawing Sheets

Specification includes a Sequence Listing.

(51) Int. Cl.
| | |
|---|---|
| C08G 77/46 | (2006.01) |
| C12N 13/00 | (2006.01) |
| G01N 33/574 | (2006.01) |
| C09C 1/30 | (2006.01) |
| C07F 7/08 | (2006.01) |

(52) U.S. Cl.
CPC . *G01N 33/54393* (2013.01); *G01N 33/57492* (2013.01); *C07F 7/081* (2013.01); *C08G 65/336* (2013.01); *C09C 1/3081* (2013.01)

(56) References Cited

U.S. PATENT DOCUMENTS

| | | | |
|---|---|---|---|
| 4,791,214 A * | 12/1988 | Mori | C08K 5/17 556/423 |
| 2009/0280063 A1 | 11/2009 | Kulkarni | |
| 2010/0143263 A1 | 6/2010 | Cheon | |
| 2010/0297026 A1 | 11/2010 | Dolye | |
| 2012/0230919 A1 | 9/2012 | Yoon | |

FOREIGN PATENT DOCUMENTS

| | | |
|---|---|---|
| WO | 2014047318 | 3/2014 |
| WO | 2014145573 | 9/2014 |

OTHER PUBLICATIONS

Bloemen et al. Heterobifunctional PEG Ligands for Bioconjugation Reactions on Iron Oxide Nanoparticles, PLoS ONE 9(10): e109475, 2014.
Chen et al. Biocompatible Polysiloxane-Containing Diblock Copolymer PEO-b-PγMPS for Coating Magnetic Nanoparticles, vol. 1, No. 10: 2134-2140, 2009.
Demirer et al. Synthesis and design of biologically inspired biocompatible iron oxide nanoparticles for biomedical applications, J. Mater. Chem. B, 2015, 3, 7831.
Jeager et al. Silicones in Industrial Applications, chapter 19. Organo-Functional Silanes, Nova Science Publishers, 2007.
Kataby et al. Self-Assembled Monolayer Coatings on Amorphous Iron and Iron Oxide Nanoparticles: Thermal Stability and Chemical Reactivity Studies, Langmuir 1997, 13, 6151-6158.
Kataby et al. Coating of Amorphous Iron Nanoparticles by Long-Chain Alcohols, Langmuir 1998, 14, 1512-1515.
Killops et al. Robust, Efficient, and Orthogonal Synthesis of Dendrimers via Thiol-ene "Click" Chemistry, J. Am. Chem. Soc. 2008, 130, 5062-5064.
Li et al. PEG-b-AGE polymer coated magnetic nanoparticle probes with facile functionalization and anti-fouling properties for reducing non-specific uptake and improving biomarker targeting, J. Mater. Chem. B, 2015, 3, 3591.
Lin et al. Improving sensitivity and specificity of capturing and detecting targeted cancer cells with anti-biofouling polymer coated magnetic iron oxide nanoparticles, Colloids and Surfaces B: Biointerfaces 150 (2017) 261-270.
Masoudi et al. The effect of poly(ethylene glycol) coating on colloidal stability of superparamagnetic iron oxide nanoparticles as potential MRI contrast agent, International Journal of Pharmaceutics 433 (2012) 129-141.
Nazli et al. Targeted delivery of doxorubicin into tumor cells via MMP-sensitivePEG hydrogel-coated magnetic iron oxide nanoparticles (MIONPs), Colloids and Surfaces B: Biointerfaces 122 (2014) 674-683.
Peng et al. Targeted magnetic iron oxide nanoparticles for tumor imaging and therapy, International Journal of Nanomedicine 2008:3(3) 311-321.
Shechter et al. Glycidyl Ether Reactions with Amines, Ind. Eng. Chem., 1956, 48 (1), pp. 94-97.
Thomas et al. Magnetic Iron Oxide Nanoparticles for Multimodal Imaging and Therapy of Cancer, Int. J. Mol. Sci. 2013, 14, 15910-15930.
Zhang et al. Gelatin—siloxane nanoparticles to deliver nitric oxide for vascular cell regulation: Synthesis, cytocompatibility, and cellular responses, J Biomed Mater Res Part A 2015:103A:929-938.

* cited by examiner

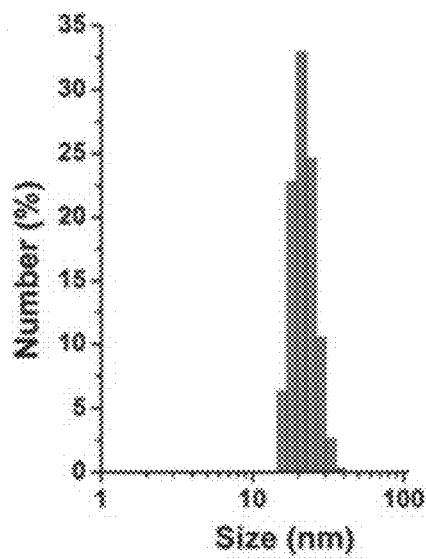 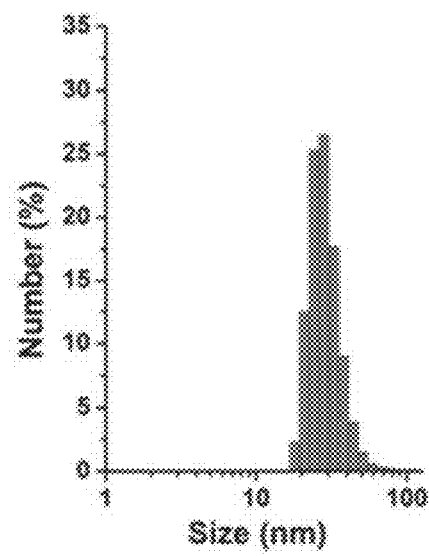
FIG. 2A　　　　　　　　　　FIG. 2B
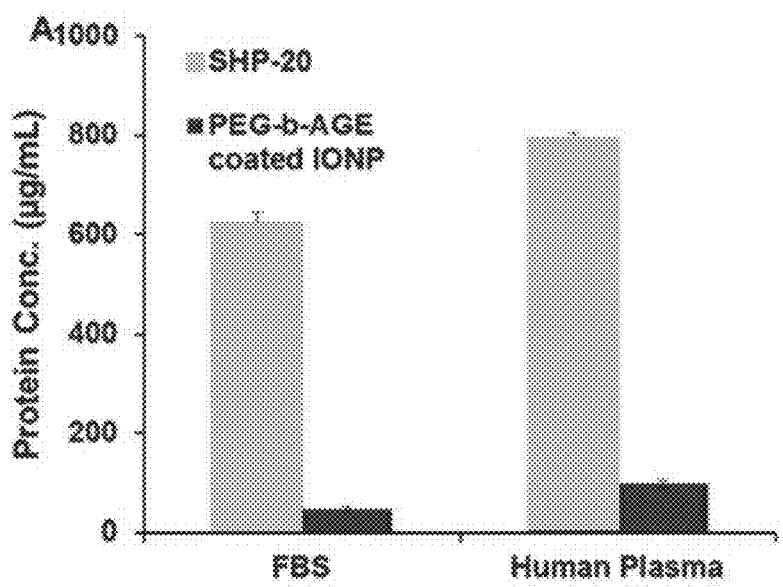
FIG. 3A

SEQUENCE LISTING

<160> NUMBER OF SEQ ID NOS: 5

<210> SEQ ID NO 1
<211> LENGTH: 4
<212> TYPE: PRT
<213> ORGANISM: Artificial
<220> FEATURE:
<223> OTHER INFORMATION: Synthetic

<400> SEQUENCE: 1

Gly Phe Leu Gly
1

<210> SEQ ID NO 2
<211> LENGTH: 4
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid

<400> SEQUENCE: 2

Gly Xaa Tyr Glx
1

<210> SEQ ID NO 3
<211> LENGTH: 135
<212> TYPE: PRT
<213> ORGANISM: Artificial
<220> FEATURE:
<223> OTHER INFORMATION: Synthetic

<400> SEQUENCE: 3

Met Arg Ala Leu Leu Ala Arg Leu Leu Leu Cys Val Leu Val Val Ser
1               5                   10                  15

Asp Ser Lys Gly Ser Asn Glu Leu His Gln Val Pro Ser Asn Cys Asp
            20                  25                  30

Cys Leu Asn Gly Gly Thr Cys Val Ser Asn Lys Tyr Phe Ser Asn Ile
        35                  40                  45

His Trp Cys Asn Cys Pro Lys Lys Phe Gly Gly Gln His Cys Glu Ile
    50                  55                  60

Asp Lys Ser Lys Thr Cys Tyr Glu Gly Asn Gly His Phe Tyr Arg Gly
65                  70                  75                  80

Lys Ala Ser Thr Asp Thr Met Gly Arg Pro Cys Leu Pro Trp Asn Ser
                85                  90                  95

Ala Thr Val Leu Gln Gln Thr Tyr His Ala His Arg Ser Asp Ala Leu
            100                 105                 110

Gln Leu Gly Leu Gly Lys His Asn Tyr Cys Arg Asn Pro Asp Asn Arg
        115                 120                 125

Arg Arg Pro Trp Cys Tyr Val
    130                 135

<210> SEQ ID NO 4
<211> LENGTH: 227
<212> TYPE: PRT
<213> ORGANISM: Artificial
<220> FEATURE:
<223> OTHER INFORMATION: Synthetic

<400> SEQUENCE: 4

```
Glu Val Lys Lys Pro Gly Ser Ser Val Lys Val Ser Cys Lys Ala Ser
1               5                   10                  15

Gly Gly Thr Phe Ser Ser Tyr Ala Ile Ser Trp Val Arg Gln Ala Pro
            20                  25                  30

Gly Gln Gly Leu Glu Trp Met Gly Gly Ile Ile Pro Ile Phe Gly Thr
        35                  40                  45

Ala Asn Tyr Ala Gln Lys Phe Gln Gly Arg Val Thr Ile Thr Ala Asp
    50                  55                  60

Glu Ser Thr Ser Thr Ala Tyr Met Glu Leu Ser Ser Leu Arg Ser Glu
65                  70                  75                  80

Asp Thr Ala Val Tyr Tyr Cys Ala Arg Thr Arg Leu Lys His Gln Trp
                85                  90                  95

Gly Gln Gly Thr Leu Val Thr Val Ser Ser Gly Gly Gly Gly Ser Gly
            100                 105                 110

Gly Gly Gly Ser Gly Gly Ser Ala Leu Ser Ser Glu Leu Thr Gln Asp
        115                 120                 125

Pro Ala Val Ser Val Ala Leu Gly Gln Thr Val Arg Ile Thr Cys Gln
130                 135                 140

Gly Asp Ser Leu Arg Ser Tyr Tyr Ala Ser Trp Tyr Gln Gln Lys Pro
145                 150                 155                 160

Gly Gln Ala Pro Val Leu Val Ile Tyr Gly Lys Asn Asn Arg Pro Ser
            165                 170                 175

Gly Ile Pro Asp Arg Phe Ser Gly Ser Ser Ser Gly Asn Thr Ala Ser
        180                 185                 190

Leu Thr Ile Thr Gly Ala Gln Ala Glu Asp Glu Ala Asp Tyr Tyr Cys
            195                 200                 205

Asn Ser Arg Asp Ser Ser Gly Pro Val Phe Gly Gly Gly Thr Lys Leu
210                 215                 220

Thr Val Leu
225

<210> SEQ ID NO 5
<211> LENGTH: 58
<212> TYPE: PRT
<213> ORGANISM: Artificial
<220> FEATURE:
<223> OTHER INFORMATION: Synthetic

<400> SEQUENCE: 5

Val Asp Asn Lys Phe Asn Lys Glu Met Arg Asn Ala Tyr Trp Glu Ile
1               5                   10                  15

Ala Leu Leu Pro Asn Leu Asn Asn Gln Gln Lys Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55
```

ANTI-FOULING SALINE AND SILOXANE COATED PARTICLES, SUBSTRATES, POLYMERS AND USES RELATED THERETO

CROSS-REFERENCE TO RELATED APPLICATIONS

This application claims priority to U.S. provisional application No. 62/317,239 filed Apr. 1, 2016. The entirety of this application is hereby incorporated by reference for all purposes.

STATEMENT REGARDING FEDERALLY FUNDED RESEARCH

This invention was made with government support under R01CA154846-02 and U01CA151810-02 awarded by NIH. The government has certain rights in the invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy, and is hereby incorporated by reference into the specification. The name of the text file containing the Sequence Listing is 15156US_ST25.txt. The text file is 5 KB, was created on Mar. 31, 2017, and is being submitted electronically via EFS-Web.

BACKGROUND

Many particle formulations, such as metal containing nanoparticles, are currently under investigation as carriers for drug delivery and as cell or biomolecule detection agents or devices for in vitro diagnostics. Ligands and specific binding agents such as antibodies are often attached to the exterior of the particles as targeting moieties for the purpose of directing the particles to diseased cells that express a binding partner. Demirer et al. report synthesis and design of iron oxide nanoparticles for biomedical applications. J. Mater. Chem. B, 2015, 3, 7831. Anbarasu et al. report synthesis and characterization of polyethylene glycol (PEG) coated $Fe_3O_4$ nanoparticles. Spectrochim. Acta, Part A, 2015, 135, 536-539. Nazli et al. report targeted delivery of doxorubicin into tumor cells via MMP-sensitive PEG hydrogel-coated magnetic iron oxide nanoparticles (MIONPs). Colloids Surf, B, 2014, 122, 674-683. See also US Patent Application Publication 2009/0280063; 20120230919; and PCT publications WO 1999/062079 and WO 2014/145573.

Chen et al. report biocompatible polysiloxane-containing diblock copolymer for coating magnetic nanoparticles. ACS Appl Mater Interfaces, 2009, 1(10):2134-40. See also Zhang et al., J Biomed Mater Res A. 2015, 103(3):929-38 and Jaeger, Silicones in Industrial Applications, Chapter 19 Silicone Organo-Functional Silane reactions, 2007.

The non-specific adsorption of bio-macromolecules in fluids on nanoparticles is known as biofouling and results in the formation of an unwanted outer layer on nanoparticle surfaces compromising the ability to specifically target cells. Thus, there is a need to find improved coatings that minimizes non-specific adsorption.

References cited herein are not an admission of prior art.

SUMMARY

This disclosure relates to polymer coatings with desirable anti-fouling properties. In certain embodiments, polymers are coated on particles, which allow for conjugation with targeting moieties. In certain embodiments, the particles are nanoparticles with targeting moieties that bind with tumor associated antigens.

In certain embodiments the disclosure relates to siloxy polymer/compounds in which the siloxy group allows for anchoring the polymer, polyethylene glycol polymer, or other compound to a substrate or particle. In other aspects, embodiments disclosed herein provide for methods comprising anchoring a substituted siloxy group to form a siloxane-coated particle surface.

In certain embodiments, the disclosure relates to siloxy polymers made by processes disclosed herein. In certain embodiment, the disclosure relates to a polymer having the following formula:

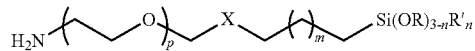

wherein p is 1 to 10,000, or 1 to 5,000, or 2 to 5,000, or 3 to 5,000, or 1 to 2,000, or 2 to 2,000, or 3 to 2,000; m is 0, 1, 2, 3, 4, 5, 6, 7, 8, 9, 10, 11, 12, 1 to 10, 1 to 22, X is —CH(OH)CH$_2$OCH$_2$CH$_2$CH$_2$S—, —CH(OH)CH$_2$OCH$_2$CH$_2$CH$_2$NH—, —CH(OH)CH$_2$OCH$_2$CH$_2$CH$_2$O—, or other linking group; n=0, 1, 2; R is an alkyl group; R' is alkyl group.

In certain embodiments, the disclosure relates to a polymer having the following formula:

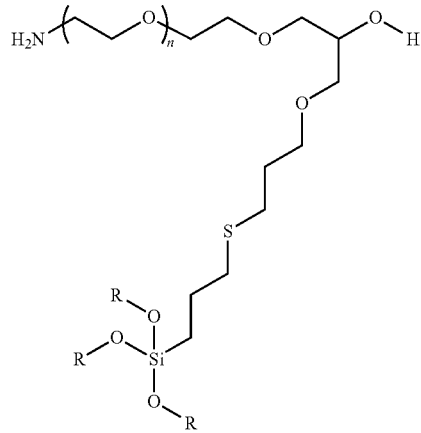

wherein R is alkyl and n is 1 to 10,000, or 1 to 5,000, or 2 to 5,000, or 3 to 5,000, or 1 to 2,000, or 2 to 2,000, or 3 to 2,000 or derivatives thereof.

In certain embodiments, this disclosure relates to polymers comprising a) linear polyalkyoxy monomers optionally comprising an alkylthio monomer or an alkylamino monomer, b) a first terminal group selected from an amine group providing an amine terminus, or a thiol group providing a thiol terminus, or a terminal hydroxyl group providing a hydroxyl terminus and c) a terminal alkoxysilane, providing a second terminus. In certain embodiments, the alkoxysilane is trimethoxysilane, triethoxysilane, tripropoxysilane, or tributoxysilane. In certain embodiments, the polymer comprises only one interior hydroxyl group. In certain embodiments, the second terminus comprises a) an alkylthio monomer terminally substituted with an alkoxysilane or b) an alkylamino monomer terminally substituted with the alkoxysilane, or c) an alkoxy monomer terminally substituted with the alkoxysilane.

In certain embodiments, the second terminus comprises the formula X—CH$_2$(CH$_2$)$_m$CH$_2$Si(OR)$_{3-n}$R'$_n$ where m is 0 or 1; n=0, 1, 2; R is an alkyl group; R' is alkyl group; and X is a linking group.

In certain embodiments, the linking group is —NH—, —CH$_2$—, —S—, —O—, —(C═O)O—, —O(C═O)—, or —(C═O)CH(CH$_3$)— or combinations thereof.

In certain embodiments, the disclosure relates to substrates coated with a polymer disclosed herein. In certain embodiments, the polymer is made by the process of mixing a substrate and the polymer under conditions such that alkoxysilane hydrolyzes to form a siloxane coating on the substrate.

In certain embodiments, the disclosure relates to particles coated with a polymer disclosed herein. In certain embodiments, the polymer-coated particle is made by the process of mixing a particle and the polymer under conditions such that siloxy coats the particles.

In certain embodiments, the particle comprises a metal, metal oxide, glass, mineral, silica, Fe, Ag, Au, or Al core. In certain embodiments, the particle core has of an average diameter of between 3 nm to 1000 nm or 3 nm to 500 nm, 3 nm to 250 nm, 3 nm to 100 nm, 3 nm to 50 nm, 3 nm to 30 nm, or 3 nm to 15 nm.

In certain embodiments, the terminal group is further conjugated to a targeting moiety. In certain embodiments, the targeting moiety is an antibody, antibody fragment, antibody mimetic, affibody, nucleic acids, oligonucleotides, aptamers, ligands, peptides, steroids, tyrosine kinase inhibitor, or non-peptidic ligand.

In certain embodiments, the particle has the following formula:

wherein at least one R is a siloxane or connecting point to the surface of the particle or particle coating.

In certain embodiments, the particle has the following formula:

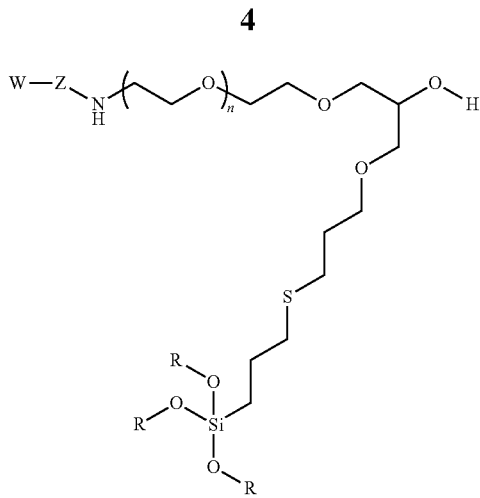

wherein W is a targeting group, Z is a linking group, R is alkyl, Si or attachment to the substrate, particle, or coating e.g., a metal at the surface of a particle, and at least one R is a siloxane or connecting point to the surface of the substrate or particle.

In certain embodiments, the particles disclosed herein may be further conjugated to pharmaceutical agents, drug molecules, proteins, ligands, polypeptides, nucleic acids, fluorescent dyes, or fluorescent proteins and vectors that express mRNA or siRNA.

In yet other aspects, embodiments disclosed herein provide a method of making particles comprised of a metal, metal oxide, non-metal oxide, or glass. The method includes mixing particles disclosed herein with a siloxy polymer disclosed herein, e.g., polymers having a terminal alkoxysilane group.

In some aspects, embodiments disclosed herein comprise a nanoparticle comprising a polymer coating. In certain aspects, embodiments disclosed herein provide a method of making siloxane-coated particles further functionalized with a targeting group moiety that combines with target cells. In some embodiments, the targeting group is transferrin or the polypeptide, RGD.

In yet other aspects, embodiments disclosed herein provide a method of separating target cells comprising mixing the a coated nanoparticle disclosed herein, e.g., target moiety-functionalized PEG-b-AGE coated nanoparticles, with a heterogeneous mixture of cells, e.g., comprising target cells and normal cells; exposing the mixture to a magnetic field, in which the magnetic nanostructures are restrained, thereby separating target cells from normal cells when the solution is removed from the area of the magnetic field.

In certain embodiments, the disclosure relates to uses of siloxane-coated particles disclosed herein for purifying target cells, detecting target cells or specific compounds of interest, in vivo or in vitro. In certain embodiments, the disclosure relates to uses of siloxane coated particles disclosed herein for imaging as contrast agents. In certain embodiments, the disclosure relates to uses of siloxane-coated particles disclosed herein for therapeutic applications such as for drug delivery and or local hyperthermia.

BRIEF DESCRIPTION OF THE DRAWINGS

FIG. 2A shows data on the hydrodynamic diameter distribution of PEG-b-AGE polymer coated IONP (with a core diameter of 10 nm).

FIG. 2B shows data on the hydrodynamic diameter distribution of) PEG-b-AGE polymer coated IONP (with a core diameter of 20 nm) measured by DLS.

FIG. 3A shows data on surface protein corona formation measurement of commercially available amphiphilic polymer coated SHP-20 (with a core diameter of 20 nm) and PEG-b-AGE polymer coated IONP quantified by BCA protein assay.

DETAILED DISCUSSION

Figure 1:
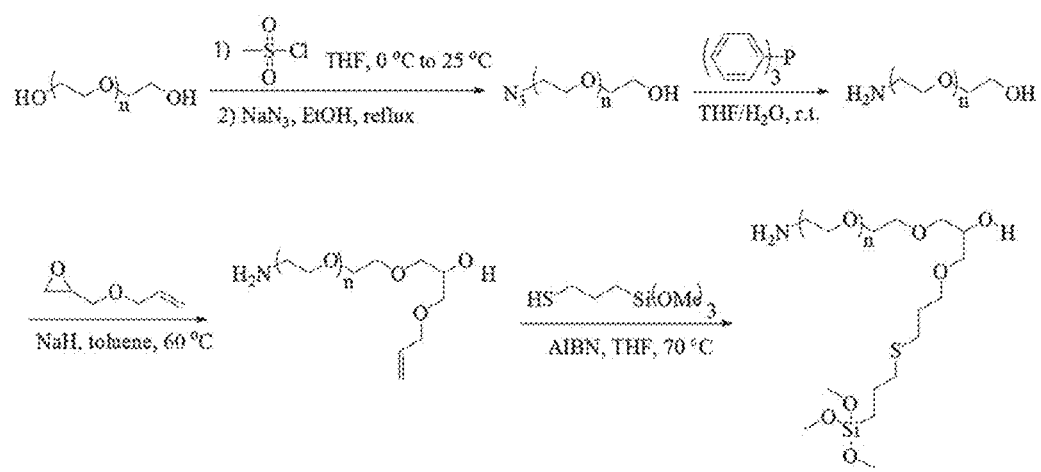
FIG. 1 illustrates the synthesis of the coating polymer PEG-b-AGE.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

To the extent that chemical formula reported herein contain one or more chiral centers, the formula are intended to encompass all stable stereoisomers, enantiomers, and diastereomers. It is also understood that formula encompass all tautomeric forms.

It must be noted that, as used in the specification and the appended claims, the singular forms "a," "an," and "the" include plural referents unless the context clearly dictates otherwise.

A "siloxane" refers to a compound with silicon to oxygen to silicon covalent bonds, and a "siloxy" group refers to a (RO)$_3$Si— group wherein R is any chemical group with at least one carbon atom covalently bound to the oxygen atom. Examples include alkyl, benzyl, and phenyl groups.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing an oxygen atom with a sulfur atom or replacing an amino group with a hydroxy group. The derivative may be a prodrug. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze, hereby incorporated by reference.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, NR$_a$R$_b$, —NR$_a$C(=O)R$_b$, —NR$_a$C(=O)NR$_a$NR$_b$, —NR$_a$C (=O)OR$_b$, —NR$_a$SO$_2$R$_b$, —C(=O)R$_a$, —C(=O)OR$_a$, —C(=O)NR$_a$R$_b$, —OC(=O)NR$_a$R$_b$, —OR$_a$, —SR$_a$, —SOR$_a$, —S(=O)$_2$R$_a$, —OS(=O)$_2$R$_a$ and —S(=O)$_2$OR$_a$. R$_a$ and R$_b$ in this context may be the same or different and independently hydrogen, halogen hydroxy, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

"Subject" refers any animal, preferably a human patient, livestock, or domestic pet.

As used herein, the terms "treat" and "treating" are not limited to the case where the subject (e.g. patient) is cured and the disease is eradicated. Rather, embodiments, of the present disclosure also contemplate treatment that merely reduces symptoms, and/or delays disease progression.

A "polymer" or "polymer coating" refers to a class of compounds in which starting materials, product, or both are combined to form repeat units. As used herein, polymers include natural polymers and modified polymers.

A "linking group" refers to any variety of molecular arrangements that can be used to bridge to molecular moieties together. An example formula may be —R$_m$— wherein R is selected individually and independently at each occurrence as: —CR$_m$R$_m$—, —CHR$_m$—, —CH—, —C—, —CH$_2$—, —C(OH)R$_m$, —C(OH)(OH)—, —C(OH)H, —C(Hal)R$_m$—, —C(Hal)(Hal)-, —C(Hal)H—, —C(N$_3$)R$_m$—, —C(CN)R$_m$—, —C(CN)(CN)—, —C(CN)H—, —C(N$_3$)(N$_3$)—, —C(N$_3$)H—, —O—, —S—, —N—, —NH—, —NR$_m$—, —(C=O)—, —(C=NH)—, —(C=S)—, —(C=CH$_2$)—, which may contain single, double, or triple bonds individually and independently between the R groups. If an R is branched with an R$_m$ it may be terminated with a group such as —CH$_3$, —H, —CH=CH$_2$, —CCH, —OH, —SH, —NH$_2$, —N$_3$, —CN, or -Hal, or two branched R's may form a cyclic structure. It is contemplated that in certain instances, the total Rs or "m" may be less than 100 or 50 or 25 or 10. Examples of linking groups include bridging alkyl groups and alkoxyalkyl groups.

"Target cells" refers to a cell containing at least one common molecule that is capable of binding with a targeting moiety. In certain embodiments, the target cell is a mammalian cell or a eukaryotic or prokaryotic cell. In certain embodiments, the targeting moiety is designed to bind with a protein or polypeptide that is expressed in a specific cell population, e.g., lymphocytes, monocytes, stem cells, or a surface marker on tumor cells.

"Target compounds" refers to a molecule containing at least one common property that enables binding of a compound with a targeting moiety. In certain embodiments, the target compound is an amyloid peptide or glucose. In certain embodiments, the targeting moiety is designed to bind with a protein or polypeptide that is released from the cells or secreted from the organs.

"Cancer" refers any of various cellular diseases with malignant neoplasms characterized by the proliferation of cells. It is not intended that the diseased cells must actually invade surrounding tissue and metastasize to new body sites. Cancer can involve any tissue of the body and have many different forms in each body area. Within the context of certain embodiments, whether "cancer is reduced" can be identified by a variety of diagnostic manners known to one skill in the art including, but not limited to, observation the reduction in size or number of tumor masses or if an increase of apoptosis of cancer cells observed, e.g., if more than a 5% increase in apoptosis of cancer cells is observed for a sample particle compared to a control without the particle. It can also be identified by a change in relevant biomarker or gene expression profile, such as PSA for prostate cancer, HER2 for breast cancer, or others.

A "chemotherapy agent," "chemotherapeutic," "anti-cancer agent" or the like, refer to molecules that are recognized to aid in the treatment of a cancer. Contemplated examples include the following molecules or derivatives such as temozolomide, carmustine, bevacizumab, procarbazine, lomustine, vincristine, gefitinib, erlotinib, cisplatin, carboplatin, oxaliplatin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin, mithramycin, vinblastine, vindesine, vinorelbine, paclitaxel, taxol, docetaxel, etoposide, teniposide, amsacrine, topotecan, camptothecin, bortezomib, anagrelide, tamoxifen, toremifene, raloxifene, droloxifene, iodoxyfene, fulvestrant, bicalutamide, flutamide, nilutamide, cyproterone, goserelin, leuprorelin, buserelin, megestrol, anastrozole, letrozole, vorozole, exemestane, finasteride, marimastat, trastuzumab, cetuximab, dasatinib, imatinib, combretastatin, thalidomide, azacitidine, azathioprine, capecitabine, chlorambucil, cyclophosphamide, cytarabine, daunorubicin, doxifluridine, epothilone, irinotecan, mechlorethamine, mercaptopurine, mitoxantrone, pemetrexed, tioguanine, valrubicin and/or lenalidomide or combinations thereof such as cyclophosphamide, methotrexate, 5-fluorouracil (CMF); doxorubicin, cyclophosphamide (AC); mustine, vincristine, procarbazine, prednisolone (MOPP); sdriamycin, bleomycin, vinblastine, dacarbazine (ABVD); cyclophosphamide, doxorubicin, vincristine, prednisolone (CHOP); bleomycin, etoposide, cisplatin (BEP); epirubicin, cisplatin, 5-fluorouracil (ECF); epirubicin, cisplatin, capecitabine (ECX); methotrexate, vincristine, doxorubicin, cisplatin (MVAC).

As used herein, the term "conjugate" refers to molecular entities joined by covalent bonds or other arrangement that provides substantially irreversible binding under physiological conditions. For example, two proteins, isolated and/or purified polypeptide sequence, may be conjugated together by a linker polymer, e.g., amino acid, polypeptide sequence, ethylene glycol polymer. Two proteins may be conjugated together by linking one protein to a ligand and linking the second protein to a receptor, e.g., streptavidin and biotin or an antibody and an epitope.

The terms "nucleic acid" refer to any nucleotide sequence (e.g., RNA or DNA), the manipulation of which may be deemed desirable for any reason (e.g., treat disease, confer improved qualities, etc.), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product (e.g., promoter sequence, polyadenylation sequence, termination sequence, enhancer sequence, etc.).

The terms "a nucleic acid sequence encoding" a specified polypeptide refer to a nucleic acid sequence comprising the coding region of a gene or in other words the nucleic acid sequence which encodes a product. The coding region may be present in a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc., may be placed in close proximity to the coding region if needed to permit proper initiation of transcription and/or correct processing of the primary RNA transcript. Alternatively, the coding region utilized in the expression vectors may contain endogenous enhancers, exogenous promoters, splice junctions, intervening sequences, polyadenylation signals, etc., or a combination of both endogenous and exogenous control elements.

As used herein, the term "exogenous promoter" refers to a promoter in operable combination with a coding region wherein the promoter is not the promoter naturally associated with the coding region in the genome of an organism. The promoter which is naturally associated or linked to a coding region in the genome is referred to as the "endogenous promoter" for that coding region.

The term "expression" when used in reference to a nucleic acid sequence refers to the process of converting genetic information encoded in a gene into RNA (e.g., mRNA, rRNA, tRNA, shRNA, or miRNA) through "transcription" of the gene (i.e., via the enzymatic action of an RNA polymerase), and into protein where applicable (as when a gene encodes a protein), through "translation" of mRNA.

The terms "in operable combination," "in operable order," and "operably linked" refer to the linkage of nucleic acid sequences in such a manner that a nucleic acid molecule capable of directing the transcription of a given gene and/or the synthesis of a desired RNA or protein molecule is produced.

Transcriptional control signals in eukaryotes comprise "promoter" and "enhancer" elements. Promoters and enhancers consist of short arrays of DNA sequences that interact specifically with cellular proteins involved in transcription (see, for e.g., Maniatis, et al. (1987) Science 236:1237; herein incorporated by reference). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Maniatis, et al. (1987), supra; herein incorporated by reference).

The terms "promoter" or "promoter sequence" refer to a DNA sequence that is located at the 5' end (i.e., precedes) of the coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of RNA from the gene. The promoter, therefore, serves as a transcriptional regulatory element and also provides a site for initiation of transcription of the gene into RNA.

The terms "variant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (in other words, additions), or both. Guidance in determining which and how many amino acid residues may be substituted, inserted or deleted without abolishing biological activity may be found using computer programs well known in the art, for example, DNAStar software. Variants can be tested in functional assays. Certain variants have less than 10%, and preferably less than 5%, and still more preferably less than 2% changes (whether substitutions, deletions, and so on). With regard to any of the sequences disclosed herein a variant may have 1, 2, or 3 substitutions which may be conserved. With regard to any of the sequences disclosed herein a variant may have 1, 2, or 3 insertions. With regard to any of the sequences disclosed herein a variant may have 1, 2, or 3 deletions. With regard to any of the sequences disclosed herein a variant may have greater than 50%, 60%, 70%, 80%, 85%, 90%, 95%, or 98% sequence identity or similarity.

As used herein sequence "identity" refers to the number of exactly matching residues (expressed as a percentage) in a sequence alignment between two sequences of the alignment. In certain embodiments, percentage identity of an alignment may be calculated using the number of identical positions divided by the greater of the shortest sequence or the number of equivalent positions excluding overhangs wherein internal gaps are counted as an equivalent position. For example the polypeptides GGGGGG and GGGGT have a sequence identity of 4 out of 5 or 80%. For example, the polypeptides GGGPPP and GGGAPPP have a sequence identity of 6 out of 7 or 85%.

In certain embodiments, for any contemplated percentage sequence identity, it is also contemplated that the sequence may have the same percentage of sequence similarity. Percent "similarity" is used to quantify the extent of similarity, e.g., hydrophobicity, hydrogen bonding potential, electrostatic charge, of amino acids between two sequences of the alignment. This method is similar to determining the identity except that certain amino acids do not have to be identical to have a match. In certain embodiments, sequence similarity may be calculated with well-known computer programs using default parameters. Typically, amino acids are classified as matches if they are among a group with similar properties, e.g., according to the following amino acid groups: Aromatic—F Y W; hydrophobic—A V I L; Charged positive: R K H; Charged negative—D E; Polar—S T N Q.

Polymer Coated Magnetic Nanoparticle Probes

Engineered nanomaterials, particularly nanoparticles, are tools for applications in molecular diagnosis, biomarker targeted imaging and delivery of therapy. An obstacle is the non-specific interaction between nanoparticles and endogenous biological materials. This biofouling effect leads to changes in the nanoparticle surface and functional properties and subsequent nanoparticle aggregation, as well as undesirable cellular uptake and immune system response. After systemic administration and in vitro applications with tissue and plasma samples, nanoparticles are subject to immediate interactions with bio-macromolecules, such as proteins in the blood, interstitial fluid, and cellular cytoplasm. The rapid nonspecific adsorption of proteins results in the formation of a protein layer, or protein corona, on the nanoparticle surface. The presence of the protein corona is responsible for the fast clearance of nanoparticles by the mononuclear phagocyte system (MPS), particularly macrophages, and the reticuloendothelial system (RES), such as the liver, spleen, and lung.

The biofouling or surface adsorption of bio-macromolecules and nonspecific uptake of nanoparticles by normal tissue and cells cause the substantial reduction in targeting efficiency and the off-target background signal in imaging, as well as unwanted toxicity to the normal tissues in biomarker targeted drug delivery applications.

In the effort to develop anti-biofouling materials, polyethylene glycol (PEG), polysaccharides and zwitterionic polymers have been investigated. Although these materials have shown the capability of reducing biofouling given their inert structures, the facile functionalization of these materials for introducing targeting ligands is challenging. Currently, the most commonly used strategy to overcome nonspecific protein adsorption and cell uptake is to graft PEG onto the nanoparticle surface, because PEG facilitates the formation of a hydrate film around the particle through hydrogen bonding with water, which attenuates the protein interactions, cell uptake, and immunogenic response. In order to immobilize targeting ligands onto nanoparticles with PEG based coating, the typical approach is to introduce additional moieties that contain reactive groups (e.g. —$NH_2$ or —COOH) for functionalization. Since surface charge may promote the phagocytosis process, the surface charge introduced from the reactive groups would "offset" the anti-biofouling effect from PEG. Hence, a coating material that bears reactive functional groups yet still exhibits anti-biofouling property is desirable.

Reported herein is an anti-biofouling amphiphilic diblock coating polymer that incorporates aminated hydrophilic PEG chains with hydrophobic allyl glycidyl ether (AGE) moieties, and can potentially control functional ligand density of the coating polymer during the polymerization of AGE through anionic ring-opening of the glycidyl group. The allyl group of AGE can be utilized for the attachment of other functional segments, e.g. anchoring groups, through the highly efficient and regioselective thiol-ene coupling reaction. This PEG-b-AGE copolymer utilizes the reactive trimethoxysilane group in one segment to "anchor" on the surface of highly size uniformed magnetic iron oxide nanoparticles (IONPs) obtained from thermo-decomposition, enabling coating and stabilization of the nanoparticles for further applications in physiological conditions.

The diblock copolymer PEG-b-AGE with capabilities of facile conjugation with different targeting ligands and reducing nonspecific protein adsorption and cell uptake has been developed to coat and stabilize IONP. This coating polymer demonstrated an excellent anti-biofouling effect to prevent the formation of protein corona and the non-specific uptake by a variety of human cancer cell lines. As a consequence of the excellent anti-biofouling property, surface functionalized PEG-b-AGE coated IONP conjugated with targeting ligands showed significantly improved targeting specificity and efficiency by reducing off-target and non-specific interactions with biological media, allows for highly specific targeted drug delivery and imaging with nanoparticles.

In certain embodiments, the disclosure relates to iron oxide nanoparticle coated in an ethylene glycol terminally substituted with a siloxane.

In certain embodiments, the iron oxide nanoparticle coated ethylene glycol substituted with a siloxane is formed by a method comprising: a) providing an iron oxide nanoparticle with one or more oleic acid residues; b) exposing the iron oxide nanoparticle to ethylene glycol substituted with a trialkoxysilane yielding a siloxane-coated iron oxide nanoparticle; and c) exposing ethylene glycol siloxane-coated iron oxide nanoparticle with a chemotherapy agent or conjugating it thereto. In certain embodiments, the coated iron oxide nanoparticles are 3-100 nm.

In certain embodiments, the coated iron oxide nanoparticle is magnetite ($Fe_3O_4$) or maghemite ($Fe_2O_3$).

In certain embodiments, the coated iron oxide nanoparticles are a superparamagnetic magnetic resonance imaging (Mill) contrast agent.

In certain embodiments, the coated iron oxide nanoparticles are further conjugated to at least one therapeutic agent, e.g., chemotherapeutic agent, an antibiotic agent, an antifungal agent, an antiparasitic agent or an antiviral agent. In certain embodiments, the coated iron oxide nanoparticles are conjugated with a targeting moiety.

Particles made by these processes can be coated with polymers disclosed herein. Processes for producing nanoparticles are reported in U.S. Pat. Nos. 9,028,875, 7,811,545, and 5,770,172. Using process provided therein, herein, or other known methods, one can substitute iron salts with other salts containing metal ions, e.g., metal salts comprising metal ions selected from the group consisting of Fe, Co, Ti, V, Cr, Mn, Ni, Cu, Zn, Y, Zr, Mo, Ru, Rh, Pd, Ag, Cd, Ce, Pt, Au, Ba, Sr, Pb, Hg, Al, Ga, In, Sn, Ge or mixtures thereof.

Hydrophobic iron oxide nanoparticles may be synthesized by thermo-decomposition of a metal oleate. A 1:3 molar mixture of the metal salt to sodium oleate may be dissolved in distilled water, hexane and ethanol with mixing until resulting in colored hexane layer. The hexane layer may be used as the metal source for thermo-decomposition wherein the metal oleate is mixed with 1-octadecene. Thereafter the reaction mixture is heated under conditions to provide metal, metal oxides, and multi-metallic oxides, e.g., typically 300-350° C. for 20-90 minutes.

Contemplated particles include gold and iron oxide nanoparticles. See Qian et al., Nature Biotechnology, 2008, 26, 83-90, Hadjipanayis et al., Cancer Research, 2010, 70(15): 6303-6312, and Peng et al., Int J Nanomedicine. 2008 September; 3(3): 311-321, all hereby incorporated by reference. A couple of approaches may be used for the chemical synthesis of contemplated gold nanoparticles. Alkanethiols may be used to stabilize gold particles. See, e.g., Brust et al., J Chem Soc, Chem Commun, 1994, 801-02 and Templeton et al., Acc Chem Res, 2000, 33, 27, all hereby incorporated by reference. In another approach, one uses sodium citrate as a reducing agent and stabilizing ligand. See Turkevich et al., Discuss Faraday Soc, 1951, 11, 55, hereby incorporated by reference. The particle size can be controlled by the gold precursor/citrate molar ratio. Kairdolf & Nie disclose the production of multidentate-protected colloidal gold nanoparticles. See J. Am. Chem. Soc. 2011, 133, 7268-7271, hereby incorporated by reference.

Nanoparticles are typically prepared with a mean particle diameter of 3 to 100 nm. Iron oxide nanoparticles (IONPs) may be prepared by aging a stoichiometric mixture of ferrous and ferric salts in aqueous media under basic conditions. Control over particle size (2-20 nm) and shape are provided by adjusting the pH, ionic strength and the concentration of the growth solution. The nanoparticles can be functionalized in situ using additives such as organic compounds (e.g. sodium citric) or polymers (e.g. dextran, polyvinyl alcohol). Other metals such as gold, cobalt, nickel, and manganese may be incorporated into the material.

High-temperature decomposition of $Fe(CO)_5$ in organic solvents is another way to prepare IONPs. Size (3-19 nm)

can be varied using alternative temperatures. Flame spray pyrolysis yields a range of magnetite, maghemite and wustite (FeO) particles IONPs. Iron precursor such as $Fe(CO)_5$ and $Fe(NO_3)_3$ may be used. Flame spray pyrolysis can be used to produce different nanoparticles ($TiO_2$, $ZrO_2$, silica, etc.) as well as hybrid particles (e.g. silica-IONPs).

Targeting Moieties

Within certain embodiments, particles with polymers disclosed herein further comprise a targeting moiety in order to target the particle to a physiological tissue or group of cells. Typically, diseased cells overexpress a specific cell surface marker, e.g., HER2 for breast cancer cells. Antibodies or other molecules with binding affinity to these markers may be conjugated to the particles in order to restrict the movement of the particle to the location of the cells after administration and exposure to a target.

Lee et al. report theranostic nanoparticles with controlled release of gemcitabine for targeted therapy using the amino terminal fragment (ATF) of the urokinase plasminogen activator (uPA). ACS Nano, 2013, 7(3):2078-89.

In certain embodiments, the coated nanoparticles disclosed herein are conjugated to a polypeptide having the amino terminal fragment (ATF) of the urokinase plasminogen activator (uPA), N-terminal 1 to 135 aa of human uPA, e.g., (SEQ ID NO: 3) MRALLARLLLCVLVVSDSKG-SNELHQVPSNCDCLNGGTCVSNKYFSNIHWCNCPK-KFG GQHCEIDKSKTCYEGNGHFYRGKASTDTMGRP-CLPWNSATVLQQTYHAHRSDALQLG LGKHNYCRNPDNRRRPWCYV or variants thereof which targets its cellular receptor, uPAR.

In certain embodiments, the targeting moiety is a monoclonal antibody to HER-2, e.g., Herceptin that targets HER-2 receptors for use in treating breast cancer. See Lee et al., Nat Med, 2007, 13:95-9; Artemov et al., Magn Reson Med, 2003, 49:403-8; and Huh et al., J Am Chem Soc, 2005, 127:12387-91, all hereby incorporated by reference in their entirety.

In certain embodiments, the targeting moiety is a monoclonal antibody-610 that targets a surface antigen for use in treating colon carcinoma. See Cerdan et al., Magn Reson Med, 1989, 12:151-63 1989, hereby incorporated by reference in its entirety.

In certain embodiments, the targeting moiety is an antibody to carcinoembryonic antigen (CEA) that targets CEA for use in treating colon tumors. See Tiefenauer et al., Magn Reson Imaging, 1996, 14:391-402, hereby incorporated by reference in its entirety.

In certain embodiments, the targeting moiety is a monoclonal antibody L6 that targets a surface antigen for use in treating intracranial tumor. See Remsen et al., Am J Neuroradiol, 1996, 17:411-18, hereby incorporated by reference in its entirety.

In certain embodiments, the targeting moiety is transferrin that targets transferrin receptor for use in treating carcinoma. See Kresse et al., Magn Reson Med, 1998, 40:236-42, hereby incorporated by reference in its entirety.

In certain embodiments, the targeting moiety is the EPPT peptide that targets underglycosylated mucin-1 antigen (uMUC-1) for use in treating breast, colon, pancreatic, and lung cancer. See Moore et al., Cancer Res, 2004, 64:1821-7, hereby incorporated by reference in its entirety.

In certain embodiments, the targeting moiety is folic acid that targets folate receptor for use in treating mouth carcinoma and cervical cancer. See Chen et al., PDA J Pharm Sci Technol, 2007, 61:303-13; Sun et al., Small, 2006, 4:372-9; and Sonvico et al., Bioconjug Chem, 2005, 16:1181-8, all hereby incorporated by reference in their entirety.

In certain embodiments, the targeting moiety is methotrexate that targets folate receptor for use in treating cervical cancer. See Kohler et al., Langmuir, 2005, 21:8858-64, hereby incorporated by reference in its entirety.

In certain embodiments, the targeting moiety is a monoclonal antibody A7 that targets colorectal tumor antigen for use in treating colorectal carcinoma. See Toma et al., Br J Cancer, 2005, 93:131-6, hereby incorporated by reference in its entirety.

In certain embodiments, the targeting moiety is chlorotoxin peptide that targets membrane-bound matrixmetalloproteinase-2 (MMP-2) for use in treating glioma. See Veiseh et al., Nano Lett, 2005, 5:1003-8, hereby incorporated by reference in its entirety.

In certain embodiments, the targeting moiety is F3 peptide that targets surface-localized tumor vasculature for use in treating glioma. See Reddy et al., Clin Cancer Res, 2006, 12:6677-86, hereby incorporated by reference in its entirety.

In certain embodiments, the targeting moiety is RGD or RGD4C that targets integrins for use in treating melanoma and epidermoid carcinoma. See Zhang et al., Cancer Res, 2007, 67:1555-62 and Uchida et al., J Am Chem Soc, 2006, 128:16626-33, both hereby incorporated by reference in their entirety.

In certain embodiments, the targeting moiety is luteinizing hormone releasing hormone (LHRH) that targets LHRH receptor for use in treating breast cancer. See Leuschner et al., Breast Cancer Res Treat, 2006, 99:163-76, hereby incorporated by reference in its entirety.

In certain embodiments, the targeting moiety is CREKA peptide that targets clotted plasma proteins for use in treating breast cancer. See Simberg et al., Proc Natl Acad Sci USA, 2007, 104:932-6, hereby incorporated by reference in its entirety.

In certain embodiments, the targeting moiety is an antibody to prostate specific membrane antigen (PSMA) that targets PSMA for use in treating prostate cancer. See Serda et al., Mol Imaging, 2007, 6:277-88, hereby incorporated by reference in its entirety.

In certain embodiments, the disclosure contemplates targeting moieties or proteins in any of the disclosed embodiments that are antibodies or fragments or chimera, antibody mimetics, or aptamers or any molecular entity that selectively binds targets that are more prevalent on cancer cells.

Numerous methods known to those skilled in the art are available for obtaining antibodies or antigen-binding fragments thereof. For example, antibodies can be produced using recombinant DNA methods (U.S. Pat. No. 4,816,567). Monoclonal antibodies may also be produced by generation of hybridomas in accordance with known methods. Hybridomas formed in this manner are then screened using standard methods, such as enzyme-linked immunosorbent assay (ELISA) and surface plasmon resonance analysis, to identify one or more hybridomas that produce an antibody that specifically binds with a specified antigen. Any form of the specified antigen may be used as the immunogen, e.g., recombinant antigen, naturally occurring forms, any variants or fragments thereof, as well as antigenic peptide thereof.

The modular structure of antibodies makes it possible to remove constant domains in order to reduce size and still retain antigen-binding specificity. Engineered antibody fragments allow one to create antibody libraries. A single-chain antibody (scFv) is an antibody fragment where the variable domains of the heavy ($V_H$) and light chains ($V_L$) are combined with a flexible polypeptide linker. The scFv and Fab fragments are both monovalent binders but they can be engineered into multivalent binders to gain avidity effects.

One exemplary method of making antibodies and fragments includes screening protein expression libraries, e.g., phage or ribosome display libraries. Phage display is described, for example, in U.S. Pat. No. 5,223,409.

In certain embodiments, the nanoparticle is conjugated to cetuximab or a single-chain Fv epidermal growth factor receptor antibody (ScFvEGFR) (SEQ ID NO: 4) EVK-KPGSSVKVSCKASGGTFSSYAISWVRQAPGQGLEW-MGGIIPIFGTANYAQKFQGRV TITADEST-STAYMELSSLRSEDTAVYYCARTRLKHQWGQGTLV-TVSSGGGGSGGGGSG GSALSSELTQDPAVSVALGQT-VRITCQGDSLRSYYASWYQQKPGQAPVLVIYGKN-NRPS GIPDRFSGSSSGNTASLTITGAQAEDEADYYCN-SRDSSGPVFGGGTKLTVL or variants thereof.

In addition to the use of display libraries, the specified antigen can be used to immunize a non-human animal, e.g., a rodent, e.g., a mouse, hamster, or rat. In one embodiment, the non-human animal includes at least a part of a human immunoglobulin gene. For example, it is possible to engineer mouse strains deficient in mouse antibody production with large fragments of the human Ig loci. Using the hybridoma technology, antigen-specific monoclonal antibodies derived from the genes with the desired specificity may be produced and selected. See U.S. Pat. No. 7,064,244.

Humanized antibodies may also be produced, for example, using transgenic mice that express human heavy and light chain genes, but are incapable of expressing the endogenous mouse immunoglobulin heavy and light chain genes. Winter describes an exemplary CDR-grafting method that may be used to prepare the humanized antibodies described herein (U.S. Pat. No. 5,225,539). All of the CDRs of a particular human antibody may be replaced with at least a portion of a non-human CDR, or only some of the CDRs may be replaced with non-human CDRs. It is only necessary to replace the number of CDRs required for binding of the humanized antibody to a predetermined antigen.

Humanized antibodies or fragments thereof can be generated by replacing sequences of the Fv variable domain that are not directly involved in antigen binding with equivalent sequences from human Fv variable domains. Exemplary methods for generating humanized antibodies or fragments thereof are provided by U.S. Pat. Nos. 5,585,089; 5,693,761; 5,693,762; 5,859,205; and 6,407,213. Those methods include isolating, manipulating, and expressing the nucleic acid sequences that encode all or part of immunoglobulin Fv variable domains from at least one of a heavy or light chain. Such nucleic acids may be obtained from a hybridoma producing an antibody against a predetermined target, as described above, as well as from other sources. The recombinant DNA encoding the humanized antibody molecule can then be cloned into an appropriate expression vector.

In certain embodiments, a humanized antibody is optimized by the introduction of conservative substitutions, consensus sequence substitutions, germline substitutions and/or backmutations. An antibody or fragment thereof may also be modified by specific deletion of human T cell epitopes or "deimmunization" by the methods disclosed in U.S. Pat. Nos. 7,125,689 and 7,264,806. Briefly, the heavy and light chain variable domains of an antibody can be analyzed for peptides that bind to MHC Class II; these peptides represent potential T-cell epitopes. For detection of potential T-cell epitopes, a computer modeling approach termed "peptide threading" can be applied, and in addition a database of human MHC class II binding peptides can be searched for motifs present in the VH and VL sequences. These motifs bind to any of the 18 major MHC class II DR allotypes, and thus constitute potential T cell epitopes.

Potential T-cell epitopes detected can be eliminated by substituting small numbers of amino acid residues in the variable domains, or preferably, by single amino acid substitutions. Typically, conservative substitutions are made. Often, but not exclusively, an amino acid common to a position in human germline antibody sequences may be used. The V BASE directory provides a comprehensive directory of human immunoglobulin variable region sequences. These sequences can be used as a source of human sequence, e.g., for framework regions and CDRs. Consensus human framework regions can also be used, e.g., as described in U.S. Pat. No. 6,300,064.

Antibody mimetics or engineered affinity proteins are polypeptide based target binding proteins that can specifically bind to targets but are not specifically derived from antibody $V_H$ and $V_L$ sequences. Typically, a protein motif is recognized to be conserved among a number of proteins. One can artificially create libraries of these polypeptides with amino acid diversity and screen them for binding to targets through phage, yeast, bacterial display systems, cell-free selections, and non-display systems. See Gronwall & Stahl, J Biotechnology, 2009, 140(3-4), 254-269, hereby incorporated by reference in its entirety. Antibody mimetics include affibody molecules, affilins, affitins, anticalins, avimers, darpins, fynomers, kunitz domain peptides, and monobodies.

Affibody molecules are based on a protein domain derived from staphylococcal protein A (SPA). SPA protein domain denoted Z consists of three α-helices forming a bundle structure and binds the Fc protion of human IgG1. A combinatorial library may be created by varying surface exposed residues involved in the native interaction with Fc. Affinity proteins can be isolated from the library by phage display selection technology. See Orlova et al., Cancer Res., 2007, 67:2178-2186, hereby incorporated by reference in its entirety. Orlova et al. report a HER2 binding affibody with picomolar affinity. Molecule Cancer Res. 2006; 66:4339.

In certain embodiments, the disclosure relates to particles disclosed herein wherein the targeting agent is a HER2 Affibody having (SEQ ID NO: 5) VDNKFNKEMRNAY-WEIALLPNLNNQQKRAFIRSLYDDPSQSANLLAEAK-KLNDAQAPK or variants thereof.

Monobodies, sometimes referred to as adnectins, are antibody mimics based on the scaffold of the fibronectin type III domain (FN3). See Koide et al., Methods Mol. Biol. 2007, 352: 95-109, hereby incorporated by reference in its entirety. FN3 is a 10 kDa, β-sheet domain that resembles the $V_H$ domain of an antibody with three distinct CDR-like loops, but lack disulfide bonds. FN3 libraries with randomized loops have successfully generated binders via phage display (M13 gene 3, gene 8; T7), mRNA display, yeast display and yeast two-hybrid systems. See Bloom & Calabro, Drug Discovery Today, 2009, 14(19-20):949-955, hereby incorporated by reference in its entirety.

Anticalins, sometimes referred to as lipocalins, are a group of proteins characterized by a structurally conserved rigid β-barrel structure and four flexible loops. The variable loop structures form an entry to a ligand-binding cavity. Several libraries have been constructed based on natural human lipocalins, i.e., ApoD, NGAL, and Tlc. See Skerra, FEBS J., 275 (2008), pp. 2677-2683, hereby incorporated by reference in its entirety.

The ankyrin repeat (AR) protein is composed repeat domains consisting of a β-turn followed by two α-helices. Natural ankyrin repeat proteins normally consist of four to six repeats. The ankyrin repeats form a basis for darpins (designed ankyrin repeat protein), which is a scaffold comprised of repeats of an artificial consensus ankyrin repeat domain. Combinatorial libraries have been created by randomizing residues in one repeat domain. Different numbers of the generated repeat modules can be connected together and flanked on each side by a capping repeat. The darpin libraries are typically denoted N×C, where N stands for the N-terminal capping unit, C stands for the C-terminal capping domain and x for the number of library repeat domains, typically between two to four. See Zahnd et al., J. Mol. Biol., 2007, 369:1015-1028, hereby incorporated by reference in its entirety.

Aptamers refer to affinity binding molecules identified from random proteins or nucleic acid libraries. Peptide aptamers have been selected from random loop libraries displayed on TrxA. See Borghouts et al., Expert Opin. Biol. Ther., 2005, 5:783-797, hereby incorporated by reference in its entirety. SELEX ("Systematic Evolution of Ligands by Exponential Enrichment") is a combinatorial chemistry technique for producing oligonucleotides of either single-stranded DNA or RNA that specifically bind to a target. Standard details on generating nucleic acid aptamers can be found in U.S. Pat. Nos. 5,475,096, and 5,270,163. The SELEX process provides a class of products, which are referred to as nucleic acid ligands or aptamers, which has the property of binding specifically to a desired target compound or molecule. Each SELEX-identified nucleic acid ligand is a specific ligand of a given target compound or molecule. The SELEX process is based on the fact that nucleic acids have sufficient capacity for forming a variety of two- and three-dimensional structures and sufficient chemical versatility available within their monomers to act as ligands (form specific binding pairs) with virtually any chemical compound, whether monomeric or polymeric.

Conjugation of Additional Molecules

In certain embodiments, the particles disclosed herein may be further conjugated to any pharmaceutical agents, peptide, nucleic acids, vectors that express mRNA or siRNA, and/or fluorescent dyes or proteins.

In certain embodiments, the disclosure contemplates linking targeting moieties and/or pharmaceutical agents to particles disclosed herein. It is contemplated that the linking groups may be biodegradable to that once the particle is located near or inside a target cell the pharmaceutical agent is released from the particle. In certain embodiments, the linking group is lysosomally degradable. Lee et al. report theranostic nanoparticles with controlled release of gemcitabine for targeted therapy. ACS Nano, 2013, 7(3):2078-89. Lammers et al., Biomaterials, 2009, 30(2):3466-3475, disclose the simultaneous delivery of doxorubicin and gemcitabine to tumors in vivo using polymeric drug carriers In certain embodiments, the pharmaceutical agent is an anticancer agent, doxorubicin, gemcitabine, an antibody or other specific binding agent that binds a tumor associated antigen, biological polymer, steroid, or other small molecule. Macromolecules are typically taken up in cells by passive or active endocytosis. Endosomes are small vesicles that engulf macromolecules. They subsequently fuse with lysosomes containing a variety of enzymes effective in environment with a low pH. An "lysosomally degradable" linker or moiety refer to a chemical combination that degrades due to an enzyme present in lysosomes, or has accelerated degradation in a low pH, i.e., pH of less than 6. A typical lysosomally degradable linker is the polypeptide GFLG (SEQ ID NO:1) that is degradable by cathepsin B. Cathepsin B can cleave a number of protein sequences. See Peterson & Meares, Bioconjugate Chem., 1998, 9(5):618-626, hereby incorporated by reference. In certain embodiments, the lysosomally degradable linker comprises the sequence GXYZ (SEQ ID NO:2) wherein G is glycine, X is any amino acid, Y is valine, isoleucine, or leucine, and Z is alanine, glycine or glutamine. Alanine-phenylalanine and alanine-alanine sequences are degradable by cathepsin B. See Jeong et al., J Controlled Release, 2009, 137:25-30. In certain embodiments, linkers with alanine-phenylalanine and alanine-alanine sequences are contemplated. In certain embodiments, the term includes linkers comprising polyethylene glycols, esters, and acetals linked through, ester, amide or ether groups. See e.g., Kwon et al., Mol. Pharm., 2005, 2 (1): 83-91. In certain embodiments, linkers with urethane or urea groups or combinations thereof are contemplated. See Ouchi & Ohya, Prog. Polym. Sci., 1995, 20:211-257. In certain embodiments, linkers without ester groups are contemplated. In certain embodiments, the lysosomally degradable moiety is substantially stable to esterases or does not contain an ester.

In certain embodiments, it is contemplated that particles disclosed herein are derivatives with nucleic acids. In certain embodiments, the amine terminus comprised a linking group that connects a DNA or RNA sequence to the polymers disclosed herein.

Cho et al. report targeted delivery of siRNA-generating DNA nanocassettes that express survivin. Small, 2013, 9(11):1964-73. In certain embodiments, this disclosure contemplates that the DNA sequence comprises a promotor sequence in operable combination with a nucleic sequence that encodes a protein of interest, fluorescent protein, or the nucleic acid sequence encodes microRNA that regulates the expression of a cancer associated gene, e.g., U6 promoter and a shRNA gene for in vivo siRNA expression.

RNA interference initially discovered in plants as Post-Transcriptional Gene Silencing (PTGS), is a highly conserved mechanism triggered by double-stranded RNA (dsRNA) and able to down regulate transcript of genes homologous to the dsRNA. The dsRNA is first processed by Dicer into short duplexes of 21-23 nt, called short interfering RNAs (siRNAs). Incorporated in RNA-induced silencing complex (RISC), they are able to mediate gene silencing through cleavage of the target mRNA.

"siRNA" or "small-interfering ribonucleic acid" refers to two strands of ribonucleotides which hybridize along a complementary region under physiological conditions. The siRNA molecules comprise a double-stranded region which is substantially identical to a region of the mRNA of the target gene. A region with 100% identity to the corresponding sequence of the target gene is suitable. This state is referred to as "fully complementary". However, the region may also contain one, two or three mismatches as compared to the corresponding region of the target gene, depending on the length of the region of the mRNA that is targeted, and as such may be not fully complementary. Methods to analyze and identify siRNAs with sufficient sequence identity in order to effectively inhibit expression of a specific target sequence are known in the art. A suitable mRNA target region would be the coding region. Also suitable are untranslated regions, such as the 5'-UTR, the 3'-UTR, and splice junctions as long as the regions are unique to the mRNA target and not directed to a mRNA poly A tail.

The length of the region of the siRNA complementary to the target, in accordance with the present disclosure, may be from 15 to 100 nucleotides, 18 to 25 nucleotides, 20 to 23 nucleotides, or more than 15, 16, 17 or 18 nucleotides. Where there are mismatches to the corresponding target region, the length of the complementary region is generally required to be somewhat longer. In certain embodiments, the RNA capable of RNA interference comprises a human survivin sequence of 18 to 25 nucleotides or greater than 15, 16, 17, or 18 nucleotides. Human survivin mRNA sequence (also known as *homo sapiens* baculoviral IAP repeat containing 5 (BIRC5) transcript variant 1) is ACCESSION NM_001168.2, available at http://www.ncbi.nlm.nih.gov/gene/332, hereby incorporated by reference. Alternatively spliced transcript variants encoding distinct isoforms have been found for this gene. This gene is a member of the inhibitor of apoptosis (IAP) gene family, which encode negative regulatory proteins that prevent apoptotic cell death.

Methods of Use

In certain embodiments, the disclosure relates to uses of siloxane-coated particles disclosed herein for purifying target cells, detecting target cells, in vivo or in vitro. In certain embodiments, the disclosure relates to uses of siloxane coated particles disclosed herein for imaging as contrast agent. In certain embodiments, the disclosure relates to uses of siloxane-coated particles disclosed herein for therapeutic applications such as for drug delivery and or local hyperthermia.

In certain embodiments, the disclosure relates to methods of separating cells comprising, a) providing a contained area comprising a nanoparticle disclosed herein; b) mixing the nanoparticles with a mixture of cells comprising target cells and non-target cells wherein target cells comprising a moiety that the targeting group binds under conditions such that the nanoparticles bind with target cells; c) exposing the contained area to a magnetic field; and d) moving then non-target cells such that the target cells are restrained to the magnetic field thereby separating non-target cells from target cells.

In certain embodiments, the disclosure relates to methods of detecting the presence of a cell in a confined area of a subject comprising, a) administering a composition comprising the nanoparticles disclosed herein under conditions such that the nanoparticle binds to target cells and exposing the confined area to magnetic field; and c) detecting the presence of the nanoparticles in the confined area.

In certain embodiments, the disclosure relates to a contained area or wells comprising a particle disclosed herein. In certain embodiments, the contained area or wells are surrounded, lined, or fabricated from material resistant to absorbing water, e.g., glass or plastic. In certain embodiments the contained area is a volume of less than 100, 50, 25, 10, 5, 4, 3, 2 or 1 cubic centimeters. In certain embodiments, there are a plurality of areas or wells, e.g., more than or at least 5, 10, 20, 40, 80, 100, 200, or 400 areas or wells within one square foot location, such as at least 80 wells within a microtiter plate. In certain embodiments, the contained area or wells further comprise a mixture of cells wherein a portion of the cells comprises a moiety that has affinity for the targeting moiety, e.g. cells express a surface marker that binds with a targeting moiety. In certain embodiments, the contained area or well(s) comprise or are placed in a magnetic field capable of restricting the movement of cells that are bound to particles disclosed herein.

In yet other aspects, embodiments disclosed herein provide a method of separating target cells comprising mixing the target group-functionalized PEG-b-AGE coated nanoparticles with a mixture of cells comprising target cells and normal cells; exposing the mixture to a magnetic field, in which the magnetic nanostructures are restrained, thereby separating target cells from normal cells.

In certain aspects, embodiments disclosed herein provide a method of detecting the presence of a cell in a confined area of a subject comprising administering a composition comprising the PEG-b-AGE coated nanoparticles under conditions such that the nanoparticle bind to target cells; exposing the confined area to magnetic field; detecting the presence of the target group functionalized PEG-b-AGE coated nanoparticles in the confined area.

In some aspects, the embodiments disclosed herein relate to methods wherein the subject is a human, animal, livestock, or domestic pet.

Advantageously, the nanostructures disclosed herein may be useful as anti-biofouling magnetic resonance imaging agents that can capture targeted circulating tumor cells (CTCs) with high sensitivity and specificity by significantly reducing the background signal of non-specific binding of non-target cells.

In certain embodiments, the disclosure contemplates using nanoparticles disclosed herein for imaging. In certain embodiments, the disclosure relates to methods of imaging comprising: a) administering nanoparticles as in disclosed herein to a subject, b) applying electromagnetic radiation to a region of the subject to be imaged, c) obtaining image data set, and d) displaying the image data set.

The term "image" and the term "imaging" can refer to a variety of information outputs and associated techniques for gathering useful information from administered nanoparticles. For example, in one form of basic imaging, spectroscopy is employed as an imaging technique to derive a general determination as to whether the concentration of nanoparticles has increased in a localized region. This is indicative of the presence of a malignancy technique for determining the presence of a malignant tumor in the body. After such a determination, further imaging can be undertaken (either contemporaneously or after a predetermined time interval) to determine the precise characteristics, size, shape, type, etc. of the area/tissue. This further imaging can employ different and/or more-sensitive imaging devices than those initially employed on the localized areas of nanoparticles. These further imaging devices may or may not be particularly sensitive to nanoparticles. Such devices include, but are not limited to MRIs, etc. as described herein. The terms "image" and "imaging" are, therefore, expressly meant to include all types of external scanning mechanisms for localizing nanoparticles.

In certain embodiments, the disclosure contemplates using nanoparticles disclosed herein for MRI. In certain embodiments, the disclosure relates to methods of MRI comprising: a) administering nanoparticles as in disclosed herein to a subject, b) applying a magnetic field and radio frequency energy to a region of the subject to be imaged, c) obtaining a magnetic resonance signal image data set, and d) displaying the image data set; wherein the magnetic resonance signal image data set is associated with distribution of the nanoparticles in the region. In certain embodiments, the methods optionally further comprises administering a contrast agent, e.g., comprising $Gd^{3+}$. In certain embodiments, the nanoparticles are iron oxide or iron oxide nanoparticles comprising Gd.

In certain embodiments, the region is the organs of the chest and/or abdomen such as the heart, liver, biliary tract, kidneys, spleen, bowel, pancreas, and adrenal glands. In certain embodiments, the region is the pelvic organs including the bladder and the reproductive organs such as the breast, uterus and ovaries in females and the prostate gland in males. In certain embodiments, the region is blood vessels, brain, and brain stem. In certain embodiments, the region is the lymph nodes. In certain embodiments the method is done to aid in the diagnoses or monitor treatment for conditions such as tumors of the chest, abdomen or pelvis; diseases of the liver, such as cirrhosis, and abnormalities of the bile ducts and pancreas; inflammatory bowel disease such as Crohn's disease and ulcerative colitis; heart problems, such as congenital heart disease; malformations of the blood vessels and inflammation of the vessels (vasculitis); or a fetus in the womb of a pregnant woman.

In certain embodiments, the region is the kidney wherein the subject is diagnosed with nephrogenic systemic fibrosis.

An MRI method produces in vivo magnetic resonance images of biological tissues sensitized with the local characteristics of nuclei, such as hydrogens in the water molecules that are excited with the imposition of a magnetic field and process simultaneously when applied with radiofrequency (RF) energy. In a typical $T_1$-weighted image, nuclei in different locations of a sample may get the RF energy and process differently in the magnetic field, producing different levels of signals that is the contrast in MRI. In $T_2$-weighted images, contrast is produced by measuring the loss of coherence or synchrony between the nuclei located in different areas of tissue or different tissue with different characteristics. In certain clinical situations, this can generate contrast between an area of pathology and the surrounding healthy tissue.

In certain embodiments, the disclosure contemplates using nanoparticles disclosed herein for magnetic resonance angiography (MRA). Generating images of blood vessels, both arteries and veins, may be based on flow effects or on contrast (inherent or pharmacologically generated). In certain embodiments, nanoparticles disclosed herein are used as intravenous contrast agents.

In certain embodiments, the disclosure contemplates using nanoparticles disclosed herein for real-time MRI, i.e., to the continuous monitoring (filming) of moving objects in real time. In certain embodiments, the disclosure contemplates using nanoparticles disclosed herein for the images produced by an MRI scanner are used to guide minimally invasive procedures or concurrent with a surgical procedure or a surgical procedure is temporarily interrupted so that images can be acquired to verify the success of the procedure or guide subsequent surgical work.

In certain embodiments, nanoparticles reported herein may be used in applications in diagnosis and treatment of certain cancers. An infusion via, for example, injection of a compound containing nanoparticles allows for imaging to be used in diagnosis, and where applicable, treatment of certain cancers. Although it is not intended the embodiments of the disclosure be limited by any particular mechanism, it is thought that the injected nanoparticles are absorbed by phagocytes. The phagocytes then collect in the cancer/tumor site, thereby producing an increased concentration of nanoparticles within the cancer site. Advantageously, this allows for detection of tumor masses and cancer cells. The phagocytes (phagocytic leukocytes) are types of cells that can migrate to the site of the malignancy and can be followed by detecting levels of nanoparticle uptake to the cells for imaging to assist in diagnosis.

Detection of ovarian cancer, for example, can be accomplished by following cells in the peritoneum as they collect at the site of the malignancy. Ovarian cancer is initially restricted to the peritoneal cavity for imaging and/or treatment purposes. Direct application into the peritoneum avoids the need for systemic nanoparticle delivery required in other forms of cancer, and bypasses the problem of nanoparticle sequestration in the lung and liver. Therefore, intraperitoneally administered nanomaterials, including iron oxide nanoparticles as described herein, are absorbed by the phagocytes. However, while the illustrative procedure is applied to organs and tissues where nanoparticles are not generally free to migrate throughout the body, it is expressly contemplated that the techniques herein can be adapted for use in a variety of organs using appropriate mechanisms to concentrate or control the migration of nanoparticles, so that targeted regions are more particularly provided with nanoparticle populations.

Several methods of detecting the levels of nanoparticles collected at the malignancy can be employed including but not limited to MRI, optical imaging, nuclear medicine and nanoparticle spectroscopy.

In certain embodiments, this disclosure relates to using nanoparticles disclosed herein for diagnosis. The nanoparticles may be selectively delivered proximate a cancer site containing cells associated with the cancer. This can be performed, for example, by directly administering a nanoparticle agent into a patient using a needle. Other techniques for administering the nanoparticle agent are apparent to those of ordinary skill. The concentration of nanoparticles administered in the agent is variable depending upon the sensitivity of the apparatus being employed, the treatment being performed, and other factors apparent to those of ordinary skill.

After the nanoparticle agent has been administered, a predetermined time period lapses to allow for uptake of the nanoparticles to the cancer cells. The predetermined time for waiting for nanoparticle uptake is highly variable depending upon the type of cancer and concentration of nanoparticles within the nanoparticle agent and can vary.

In certain embodiments, the disclosure contemplates treatment using nanoparticles disclosed herein. A nanoparticle-based agent administered as described herein may be further used in the treatment of cancer cells. The procedure provides for by directing an agent containing nanoparticles to be selectively delivered to a cancer site. The cancer site contains cells associated with a cancer, which selectively uptake the nanoparticles delivered in the agent. After a predetermined time period is specified to allow for uptake of the nanoparticles into the cancer cells, a field is applied to the nanoparticles for a sufficient period of time to activate the magnetic cores of the nanoparticles. This thereby induces hyperthermia-mediated destruction of the cells by heating up the nanoparticles, and more particularly the magnetic cores of the nanoparticles. The cancer cells are specifically targeted, as they uptake higher concentrations of the nanoparticles. Accordingly, the cancer cells that have taken up the nanoparticles can be destroyed by thereafter heating the nanoparticles.

In certain embodiments, the disclosure relates to methods of treating a disease or condition comprising administering an effective amount a pharmaceutical composition comprising a siloxane coated particle disclosed herein wherein the polymer is conjugated to a cell-targeting molecule to a subject in need thereof. The particles of the present disclosure can be administered to a subject either alone or as a part of a pharmaceutical composition.

In certain embodiments, the disease or condition is cancer and the subject is diagnosed with cancer. In certain embodiments, the cancer is breast or pancreatic cancer. In certain embodiments, the disclosure relates to treating or preventing cancer with particles disclosed herein wherein the cancer is selected from brain, lung, cervical, ovarian, colon, breast, gastric, skin, ovarian, pancreatic, prostate, neck, and renal cancer.

Optionally, the particles are administered in combination with a second anticancer agent. The second anticancer agent may be selected from temozolamide, bevacizumab, procarbazine, lomustine, vincristine, gefitinib, erlotinib, docetaxel, cis-platin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin and mithramycin, vinblastine, vindesine, vinorelbine, taxol, taxotere, etoposide, teniposide, amsacrine, topotecan, camptothecin, bortezomib, anagrelide, tamoxifen, toremifene, raloxifene, droloxifene, iodoxyfene, fulvestrant, bicalutamide, flutamide, nilutamide, cyproterone, goserelin, leuprorelin, buserelin, megestrol, anastrozole, letrozole, vorazole, exemestane, finasteride, marimastat, trastuzumab, cetuximab, dasatinib, imatinib, combretastatin, thalidomide, and/or lenalidomide or combinations thereof.

In certain embodiments, the disclosure contemplates imaging and effecting cell lysis with particles using iron or iron oxide cores. See WO2009/120702.

In certain embodiments, the disclosure relates to targeting of cancer by local hyperthermia using composition and methods disclosed herein. Local hyperthermia can lead to induction of apoptosis, heat-shock protein release, and chemotherapy agent sensitivity of cancer cells by exposure of cancer cells containing particles with an iron or iron oxide core to an alternating magnetic fields (<1000 kHz) that are safe to normal cells.

In certain embodiments, the disclosure relates to methods for lysis of a cancer cells comprising, administering to a subject particles disclosed herein and adjusting magnetic fields proximate the subject to cause cell lysis of cancer cell that absorb the particles after administration. Typically, the magnetic field is an oscillating magnetic field and the particles are heated to at least 37° C. in vivo typically greater than 41° C.

Magnetic Resonance Imaging (MRI)

Atomic isotopes that contain an odd number of protons, such as the hydrogen nuclei in water molecules, spin and generate magnetic fields (magnetic moment). Ferromagnetic materials, e.g., iron, lanthanide elements such as gadolinium, or Gd, and materials with magnetic moments can be used to enhance the contrast and differentiate spatial features of the image in magnetic resonance imaging (MRI) where an external magnetic field is applied to a region of the subject to be imaged. Radio frequency (RF) energy is then applied to this region. The RF energy excites the nuclei of the molecules within the tissues of the subject in a magnetic field, e.g., the hydrogen nuclei in water molecules. The excited nuclei spin emit resonating RF signals, referred to herein as magnetic resonance signals. By applying magnetic field gradients so that the magnitude of the magnetic field varies with location within the body of the subject, the magnetic resonance phenomenon can be limited to only a particular volume or "slice" of the body, so that all of the magnetic resonance signals come from that volume or slice. Moreover, by applying additional magnetic field gradients, the frequency and phase of the magnetic resonance signals from different locations within the volume or slice can be made to vary in a predictable manner depending upon the position within the slice. Stated another way, the magnetic resonance signals are "spatially encoded," so that it is possible to distinguish between signals from different parts of a slice.

If this process is repeated numerous times to elicit signals using different gradients, it is possible to derive a set of information which indicates one or more characteristics of magnetic resonance signals from particular locations within the body of the subject. Such a set of information is referred herein to as an image data set. Because the characteristics of the magnetic resonance signals vary with the concentration of different chemical substances and other chemical characteristics of the tissues, different tissues provide different magnetic resonance signal characteristics. When a magnetic resonance signal image data set is displayed in a visual format, such as on a computer screen or printed image, the information forms a picture of the structures within the body of the subject, with different tissues having different intensities or colors.

Typically, a magnetic resonance image data set is stored as a set of individual data elements. The data in each element represents one or more characteristics of magnetic resonance signals from a small volume element or "voxel." For example, the map can be stored as a three-dimensional array of data elements, the dimensions of the array corresponding to three-dimensional space. Data elements corresponding to a given plane in three-dimensional space can be selected for display in a two-dimensional picture such as a screen display or printed image. Each small area element on the surface of the picture, commonly referred to as a "pixel," is assigned an intensity or color value based on the numerical values of the data element for the corresponding voxel.

Image contrast may be weighted to demonstrate different anatomical structures or pathologies. Each tissue returns to its equilibrium state after excitation by the independent processes of $T_1$ (spin-lattice) and $T_2$ (spin-spin) relaxation. To create a $T_1$-weighted image magnetization is allowed to recover before measuring the MR signal by changing the repetition time (TR). To create a $T_2$-weighted image magnetization is allowed to decay before measuring the MR signal by changing the echo time (TE).

Magnetic resonance imaging can show abnormal tissues in contrast to surrounding normal tissues. For example, magnetic resonance signals from malignant tumors have a characteristic referred to as the spin-lattice relaxation time or "$T_1$" different from the $T_1$ of normal tissues. If a magnetic resonance image is taken so that the data in each data element depends at least in part on the $T_1$ of the tissue at the corresponding location, a picture showing malignant tumor tissue in contrast to normal tissue can be displayed.

Pictures derived from MRI images are typically read by a physician visually examining the picture to diagnose disease which may be present or to evaluate the progress of a known disease. Such evaluation may involve, for example, a mental comparison by the physician with pictures the physician has previously seen of normal and other diseased subjects or pictures taken in the past of the same subject. In this process, the physician typically attempts to discern the outlines of body structures in the picture. This may also be an automated process in which the computer examines a new image to extract "features relating to particular disease states" using a pattern recognition technique and stores signals descriptive of these features in a "fact database." These "feature signals" are compared with similar "feature signals" extracted from previously acquired images and the resulting comparison information is subjected to artificial intelligence rules to provide "a diagnostic assessment."

Typically the MRI apparatus includes an external magnet, gradient coils, a transmitter and a receiver, which themselves may be of the conventional types used in magnetic resonance imaging apparatus, as well as a system controller linked to the gradient coils, transmitter and receiver, the system controller being operative to actuate the gradient coils, transmitter and receiver to perform the sequence of operations required to elicit magnetic resonant signals from a subject in the subject receiving space, commonly referred to as a "pulse sequence." Most desirably, the support controller is operatively associated with the system controller so that magnetic resonance signals are elicited. Typically the apparatus can automatically move the subject and automatically acquire magnetic resonance data sets in a variety of subject positions. Magnetic resonance imaging includes the steps of automatically moving the subject through a pre-selected sequence of dispositions relative to a static field magnet, e.g., without moving parts of the subject relative to one another. The moving step is performed so that in at least a plurality of the pre-selected dispositions the subject is subjected to a static field provided by the static field magnet. Magnetic resonance signals are elicited from the subject in the plurality of pre-selected dispositions.

As mentioned above, use of the comparison image data set in a visual display, either by display of the comparison image data set itself or by using the comparison image data set to highlight a visually-perceptible image generated from another data set allows use of the comparative data without reliance on artificial intelligence or automated pattern recognition schemes. However, such schemes may be applied to the image data set. Merely by way of example, the system may find the dimensions of any region of contiguous voxels in the comparison image data set having non-zero values, or values above a selected threshold. Similarly, the comparison image data set can be processed to provide additional information. For example, the comparison image data set may be subjected to an automated feature-extraction process to find characteristics of the comparison image data set or of particular portions of the difference, features such as the ratio of dimensions can be found for each such region. These and other features can be extracted and compared with known disease patterns either in a rule-based system or by a neural network or other system capable of learning by exposure to a known learning set of comparison images.

The magnetic resonance data can in one or more of the image data sets can be examined automatically to select data elements corresponding to one or more particular tissue types, and the highlighting step can be limited to regions of the displayed image corresponding to particular tissue types. For example, in studies of the spine, only those pixels corresponding to voxels including disc tissue may be highlighted.

While the discussion above refers to gathering information for the voxels within a single slice of tissue, each image data set typically includes information for voxels in numerous slices, and hence each image data set includes information for voxels in a three-dimensional array of voxels.

MRI can be applied using a static field magnet incorporating physical poles aligned on a polar axis, and the field surrounds the polar axis or applied using other types of magnets as, for example, magnets which use electromagnet coils to form the static magnetic field. For example, certain magnets can include a set of superconducting main field coils held in spaced-apart relationship to one another so as to provide a subject receiving space between them. Auxiliary or "bucking" coils may be provided in association with the main field coils. The coils are arrayed along a horizontal coil axis or field axis. In known manner, the numbers of turns in the coils, the sense of the current flowing within such turns and the magnitude of such currents or selected so as to provide a substantially uniform field directed along the field axis within an imaging region or inside the subject receiving space and to suppress "fringe" fields outside of the subject receiving space. Such a magnet typically does not incorporate a ferromagnetic frame or physical poles. Such a magnet can provide a field of similar orientation and configuration to the magnets discussed above. The term "field axis" as used herein refers generally to an axis such that the field vector of the static magnetic field is parallel to the axis, and the field surrounds the axis. Stated another way, the field axis extends through the subject-receiving space of the magnet. In a magnet having poles, the field axis typically is coincident with the polar axis.

Iron oxide nanoparticles (IONPs) contain maghemite and magnetite and are ferromagnetic. The techniques of monitoring hydrogen nuclei in water by MRI can be applied to obtain the improved images when nuclei affected by ferromagnetic contrast agents, e.g., the IONPs reported herein, so as to monitor changes in the shape of a body cavity filled with the agents. Where a contrast agent is employed, the comparison image data set can be revised to eliminate voxels, which do not contain the contrast agent, and thereby limit highlighting in the displayed image to only pixels showing the contrast agent. In general, iron oxide nanoparticles require stabilization in order to prevent aggregation. IONPs with core sizes larger than 10 nm can lead to so-called T2 contrast, or signal darkening or hypointensity.

Gadolinium (III) containing MRI contrast agents are typically used for enhancement of vessels in MR angiography or for tumor enhancement, e.g., a brain tumor associated with the degradation of the blood-brain barrier. Gd(III) chelates do not pass the blood-brain barrier because they are hydrophilic. Thus, these are useful in enhancing lesions and tumors where the Gd(III) leaks out. Contemplated agents include gadoterate, gadodiamide, gadobenate, gadopentetate, gadoteridol, gadofosveset, gadoversetamide, gadoxetate, and gadobutrol. In certain embodiments, the disclosure contemplates that the nanoparticles reported herein, e.g., IONPs reported herein, can be used instead of or in combination with the Gd(III) containing MRI contrast agents in such methods. For example, contrast agent(s) are injected into a tumor or a vein. A magnetic resonance angiography is then obtained to look at the amount of blood going through different parts of the brain and/or tumor. In contrast with IONPs, Gd(III) based agents cause mostly $T_1$ contrast, or signal increasing or hyperintensity, in the affected anatomic region or abnormal tissues.

Pharmaceutical Compositions

In certain embodiments, the disclosure relates to pharmaceutical compositions comprising particles disclosed herein and a pharmaceutically acceptable excipient. In certain embodiments, the composition is a pill or in a capsule or the composition is an aqueous buffer, e.g., isotonic phosphate buffer for a pH between 6 and 8. In certain embodiments, the pharmaceutically acceptable excipient is selected from a filler, glidant, binder, disintegrant, lubricant, and saccharide. Optionally, the pharmaceutical composition further comprises a second anticancer agent.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents solvents or vehicles include water, ethanol, polyols (propylene glycol, polyethylene glycol, glycerol, and the like), suitable mixtures thereof, vegetable (such as olive oil, sesame oil and viscoleo) and injectable organic esters such as ethyl oleate.

Prevention of the action of microorganisms may be controlled by addition of any of various antibacterial and antifungal agents, example, parabens, chlorobutanol, phenol, sorbic acid, and the like. It may also be desirable to include isotonic agents, for example saccharides or polysaccharides, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders and granules. In such solid dosage forms, the particles may be admixed with at least one inert customary excipient (or carrier) such as sodium citrate or dicalcium phosphate or: (a) fillers or extenders, as for example, starches, lactose, sucrose, glucose, mannitol and silicic acid, (b) binders, as for example, carboxymethylcellulose, alginates, gelatin, polyvinylpyrrolidone, sucrose, and acacia, (c) humectants, as for example, glycerol (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar and as high molecular weight polyethylene glycols, and the like.

Solid dosage forms such as tablets, capsules, pills, and granules can be prepared with coatings and shells, such as enteric coatings and others well known in the art. They may contain opacifying agents, and can also be of such composition that they release the particles in a certain part of the intestinal tract in a delayed manner. Examples of embedding compositions, which can be used are polymeric substances and waxes.

Liquid dosage forms for oral administration include pharmaceutically acceptable emulsions, solutions, suspensions, syrups, and elixirs. In addition to the particles, the liquid dosage forms may contain inert diluents commonly used in the art, such as water or other solvents, solubilizing agents and emulsifiers, for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, viscoleo, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents. Suspensions, in addition to the particles, may contain suspending agents, as for example, ethoxylated iso-stearyl alcohols, polyoxyethylene sorbitol and sorbitan esters, microcrystalline cellulose, aluminum metahydroxide, bentonite agar-agar and tragacanth, or mixtures of these substances, and the like.

Pharmaceutical compositions typically comprise an effective amount of particles and a suitable pharmaceutical acceptable carrier. The preparations can be prepared in a manner known per se, which usually involves mixing the particles according to the disclosure with the one or more pharmaceutically acceptable carriers and, if desired, in combination with other pharmaceutical active compounds, when necessary under aseptic conditions. Reference is made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

The pharmaceutical preparations of the disclosure are preferably in a unit dosage form, and can be suitably packaged, for example in a box, blister, vial, bottle, sachet, ampoule or in any other suitable single-dose or multi-dose holder or container (which can be properly labeled); optionally with one or more leaflets containing product information and/or instructions for use. Generally, such unit dosages will contain between 1 and 1000 mg, and usually between 5 and 500 mg, of the particles of the disclosure e.g., about 10, 25, 50, 100, 200, 300 or 400 mg per unit dosage.

The particles can be administered by a variety of routes including the oral, ocular, rectal, transdermal, subcutaneous, intravenous, intramuscular or intranasal routes, depending mainly on the specific preparation used. The particles will generally be administered in an "effective amount," by which it is meant any amount of particles that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the subject per day, more often between 0.1 and 500 mg, such as between 1 and 250 mg, for example about 5, 10, 20, 50, 100, 150, 200 or 250 mg, per kilogram body weight of the subject per day, which can be administered as a single daily dose, divided over one or more daily doses. The amount(s) to be administered, the route of administration and the further treatment regimen can be determined by the treating clinician, depending on factors such as the age, gender and general condition of the subject and the nature and severity of the disease/symptoms to be treated.

Kits

In certain embodiments, the disclosure relates to kit comprising a polymer, substrate, particle, and/or coated particle disclosed herein. In certain embodiments, the kit comprises a siloxy polymer disclosed herein in a container sealed to prevent moisture from coming in contact with the polymer wherein the kit further optionally comprises a nanoparticle, e.g. an iron oxide nanoparticle disclosed herein. In certain embodiments, the kit comprises written instructions to mix the polymer and the particles under conditions such that a siloxane-coated polymer is formed.

In certain embodiments, kit comprises a polymer coated nanoparticle disclosed herein contained in a buffered aqueous solution. The solution may contain saline, be isotonic, or comprise one or more saccharides or polysaccharides. In certain embodiments, the kit comprises a siloxane polymer coated iron oxide nanoparticle linked with at least one chemotherapeutic agent.

EXPERIMENTAL

Synthesis of $NH_2$-PEG (1)

As shown in FIG. 1, PEG 1000 (4.0 g, 4 mmol, dried by vacuum at 40 1 C for 3 hours) was dissolved in distilled THF (50 mL) under argon atmosphere. The solution was cooled to 0° C. using an ice/water bath, before methanesulfonyl chloride (0.50 mL, 6.0 mmol) was added by syringe. Triethylamine (1.25 mL, 9.0 mmol) was then slowly introduced by syringe with immediate formation of a white precipitate. The mixture was allowed to warm to room temperature and stirred overnight under argon. The reaction contents were concentrated and dissolved in ethanol (75 mL). Sodium azide (2.60 g, 40.0 mmol) was then added to the solution, and the reaction was heated to reflux for 18 hours. After cooling, the solvent was removed under reduced pressure. The residue was dissolved with deionized water, transferred to a separatory funnel, and extracted with DCM three times. The combined organic layers were dried over anhydrous $Na_2SO_4$, filtered, and concentrated by rotary evaporator. The residue was dissolved in THF (100 mL), and deionized water (20 mL) was added along with triphenylphosphine (5.33 g, 20 mmol). The reaction was stirred at room temperature overnight. The reaction contents were then concentrated, dissolved in a 0.1 M NaOH aqueous solution, and transferred to a separatory funnel. The solution was washed with a diethyl ether/hexane (80/20) solution, and then extracted with DCM three times. The combined organic layers were dried over anhydrous $Na_2SO_4$, then filtered, and concentrated. The residue was recrystallized from ethyl acetate-hexane to yield white waxy solid (77.5% yield). $^1$H NMR (CDCl$_3$) d 3.70-3.54 (complex m, 84H), 2.89 (br, s, 1H), 2.50 (br, s, 2H) ppm; 13C NMR d 74.12, 72.68, 70.79, 70.74, 70.53, 61.88, 42.44 ppm. MALDI peak mass (m/z) found: 920 g mol$^{-1}$ (n=20+Na).

Synthesis of $NH_2$-PEG-AGE (2)

$NH_2$-PEG (1 g, 1 mmol) was dissolved in toluene (30 mL) under argon atmosphere. NaH (36 mg, 1.5 mmol) was then added to the solution. The reaction was heated to 60° C. for 1 hour. Allyl glycidyl ether (0.15 mL, 1.1 mmol) was introduced by syringe to the solution. The reaction was heated up to reflux for 12 hours. The reaction contents were concentrated. The residue was dissolved in the minimal amount of isopropyl alcohol, transferred to a centrifuge tube, and precipitated by addition of cold diethyl ether (−20° C.). The mixture was kept in −20° C. freezer overnight. The mixture was centrifuged, and the supernatant was decanted. The precipitation was repeated twice more, and the solid residue was lyophilized to yield brown solid (94% yield). 1H NMR (CDCl3) d 5.91-5.80 (m, 1H), 5.22 (d, 1H), 2.12 (d, 1H), 3.95 (d, 2H), 3.74-3.42 (complex m, 88H) ppm. 13C NMR d 134.86, 117.34, 74.03, 72.58, 70.71, 70.70, 70.48, 42.26 ppm. MALDI peak mass (m/z) found: 1034 g mol$^{-1}$ (n=20+Na).

Synthesis of Diblock Copolymer PEG-b-AGE (3)

The flask containing $NH_2$-PEG-AGE (0.22 g, 0.2 mmol), AIBN (11 mg, 0.066 mmol), and (3-mercaptopropyl) trimethoxysilane (0.40 mL, 2 mmol) was degassed for 15 min by vacuum, and then distilled THF (20 mL) was added by syringe under argon atmosphere. The reaction was heated up to 70° C. for 24 hours. The reaction contents were then concentrated and the residue was washed by hexane for several times to remove the unreacted (3-mercaptopropyl) trimethoxysilane. The washed residue was dried under vacuum to yield light-yellow solid (81% yield). $^1$H NMR (CDCl$_3$) d 3.70-3.38 (complex m, 104H), 2.58-2.50 (m, 4H), 1.84 (m, 2H), 1.69 (m, 2H), 0.75 (t, 2H) ppm. $^{13}$C NMR d 72.40, 71.04, 70.44, 43.01, 35.48, 32.06, 30.26, 29.07, 28.08, 14.61, 9.09 ppm.

Coating and Stabilizing IONPs with Diblock Polymer PEG-b-AGE

Figure 6:
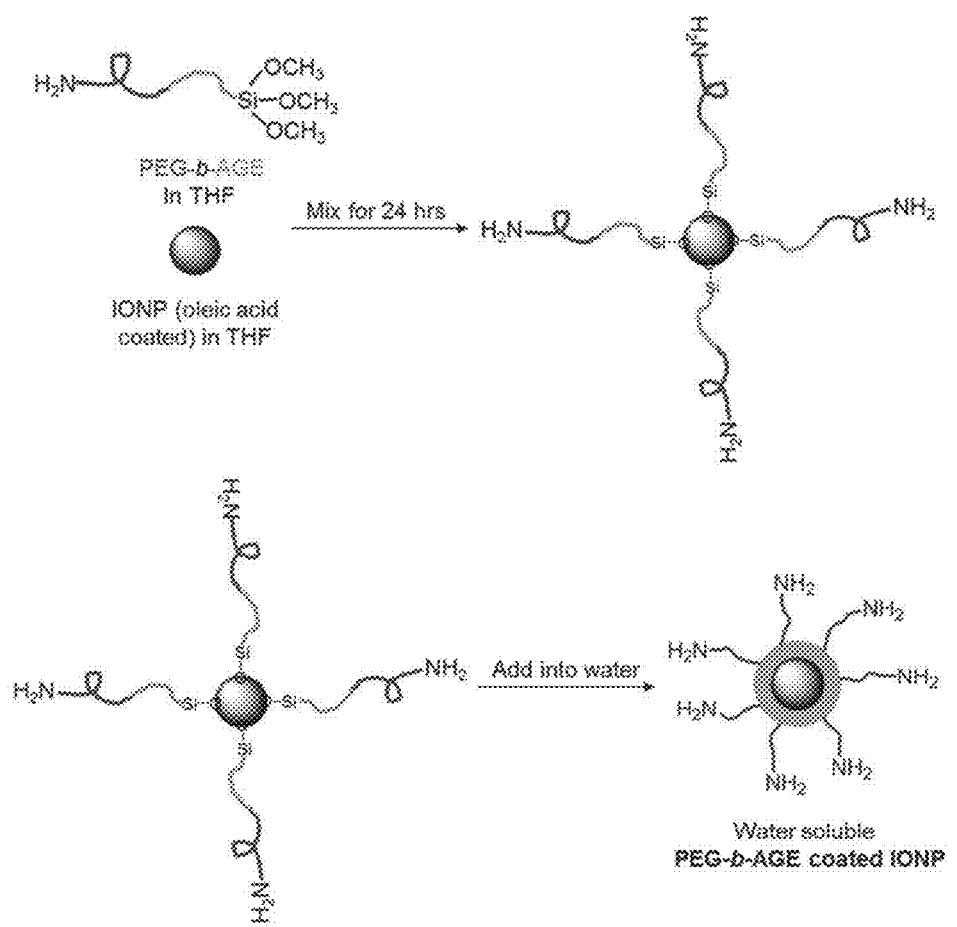
FIG. 6 shows a scheme for the preparation of water soluble PEG-b-AGE coated IONP.

PEG-b-AGE copolymer was then applied to coat hydrophobic IONPs in the organic solvent based as illustrated in FIG. 6. Oleic acid coated IONPs (10 mg, with a core diameter of 10 nm or 20 nm) were dispersed in THF (2 mL). The IONP THF solution was added to the PEG-b-AGE solution in THF (18 mL, 5 mg mL$^-$), and stirred for 24 hours at room temperature, allowing for exchange of oleic acids on the IONP surface with PEG-b-AGE polymers. The mixture was then added dropwise to deionized water (200 mL). The resultant solution was dialyzed against water for 48 hours to remove THF and unreacted polymer. The aqueous solution was then centrifuged at 3000 rpm for 5 min to eliminate any large aggregates, yielding the PEG-b-AGE coated IONP final product.

Characterization of PEG-b-AGE Coating Polymer

The PEG-b-AGE diblock polymer was obtained successfully with the procedure described in FIG. 1. The anionic ring opening employed in the synthesis of $NH_2$-PEG-AGE provides control over the number of AGE molecules attached to the PEG chain with Low PDIs. The number of AGE moieties in each PEG-b-AGE polymer would further affect the surface charge and ligand density after the nanoparticle is coated with the PEG-b-AGE polymer. The anionic ring-opening step attenuates the surface property of the PEG-b-AGE coated nanoparticles. The thiol-ene coupling reaction between the $NH_2$-PEG-AGE and the 3-mercaptopropyl trimethoxysilane took place in a regioselective fashion in the presence of AIBN. The radical addition of the thiol group from the 3-mercaptopropyl trimethoxysilane to the allyl group from the $NH_2$-PEG-AGE led to the PEG-b-AGE polymer as the only product. The trimethoxysilane group in the PEG-b-AGE polymer functions as an "anchor" that attaches the polymer onto the surface of IONPs, while the —$NH_2$ group in the other segment enables the coupling with the selected functional modality.

Coating IONPs with Diblock PEG-b-AGE Polymer

After coating the hydrophobic oleic acid attached IONPs with PEG-b-AGE polymer, the hydrophobic block of the coating polymer collapsed onto the surface of IONPs once exposed to water, resulting in a self-assembled hydrophobic layer to protect the iron oxide nanocrystal core. Meanwhile, the outer layer formed from the hydrophilic block led the resultant PEG-b-AGE polymer coated IONPs to be monodispersed in water, preventing the particles from aggregation. PEG-b-AGE polymer coated IONPs with core diameters of both 10 nm and 20 nm were highly monodispersed in water. A thin polymer layer around the core of the IONPs can be observed in the TEM images. The thickness of the coating polymer layer is estimated to be 2.5 nm based on the measurements from TEM images. The average hydrodynamic diameters (DO of the PEG-b-AGE polymer coated IONPs with core diameters of 10 nm and 20 nm were measured at 22.4 nm and 30.5 nm, respectively (Table 1).

|  |  | PEG-b-AGE coated IONP | RGD-IONP | Tf-IONP |
|---|---|---|---|---|
| 10 nm core | ζ-potential (mV) | 1.85 ± 0.42 | −3.30 ± 1.25 | −6.69 ± 0.84 |
|  | $D_H$ (nm) | 22.4 ± 0.6 | 24.7 ± 4.3 | 44.0 ± 7.3 |
| 20 nm core | ζ-potential (mV) | 17.08 ± 2.06 | −8.87 ± 0.06 | −24.60 ± 3.82 |
|  | $D_H$ (nm) | 30.5 ± 1.6 | 33.6 ± 6.4 | 48.7 ± 6.9 |

The polydispersity indexes (PDIs) are 0.213 for a nanoparticle with a core size of 10 nm and 0.225 for that with core size of 20 nm. The low PDI values of the hydrodynamic diameter measurements indicate narrow size distributions of PEG-b-AGE polymer coated IONPs. The number of surface —NH$_2$ groups for each particle was determined using the ninhydrin colorimetric method, and found to be 606±84 and 1720±214 for the PEG-b-AGE polymer coated IONP with core diameters of 10 nm and 20 nm respectively.

Conjugation of Targeting Ligands to the PEG-b-AGE Polymer Coated IONPs

Figure 7:
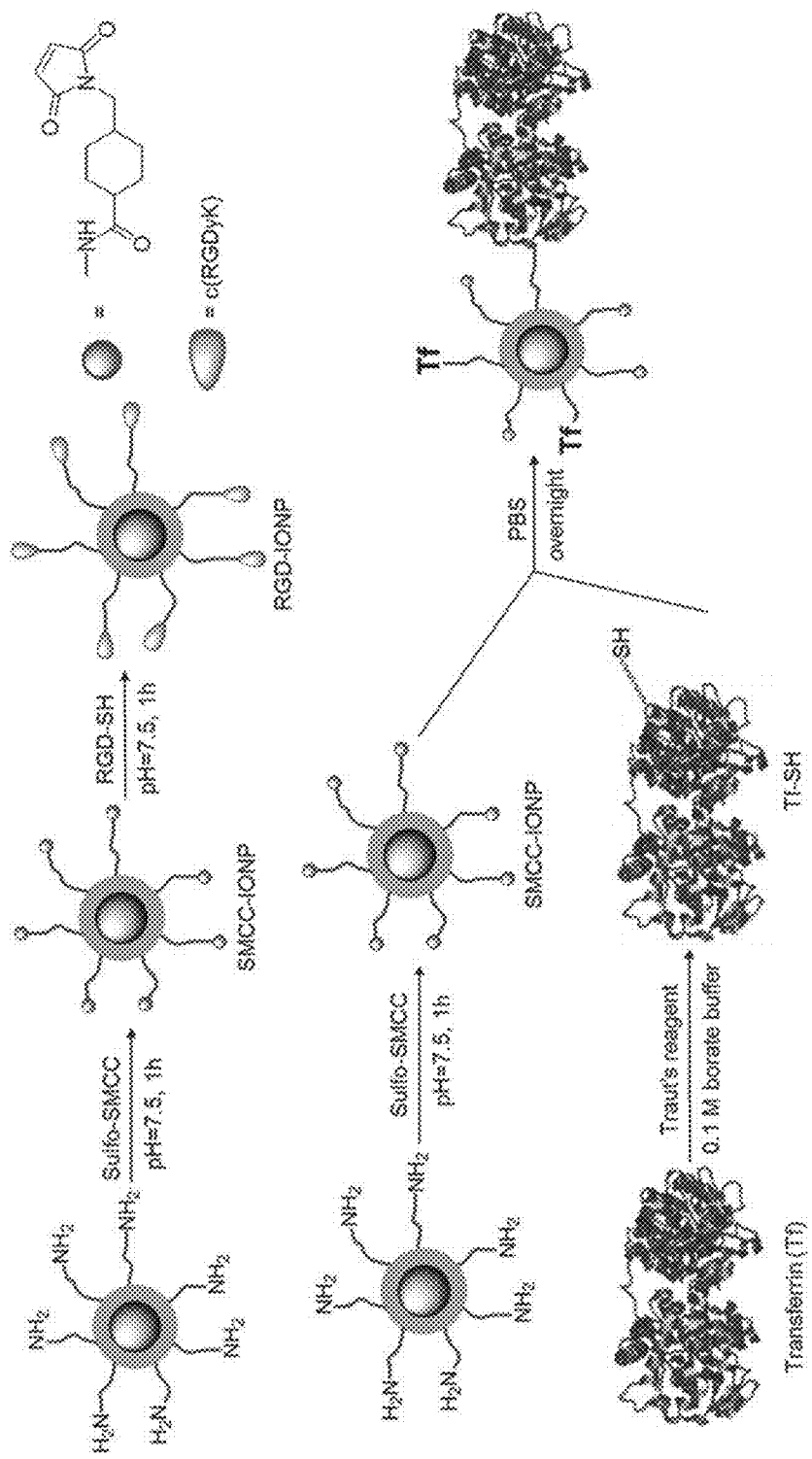
FIG. 7 shows illustration of PEG-b-AGE coated IONP conjugating with RGD ligand, and transferrin (Tf) ligand.
Figure 8:
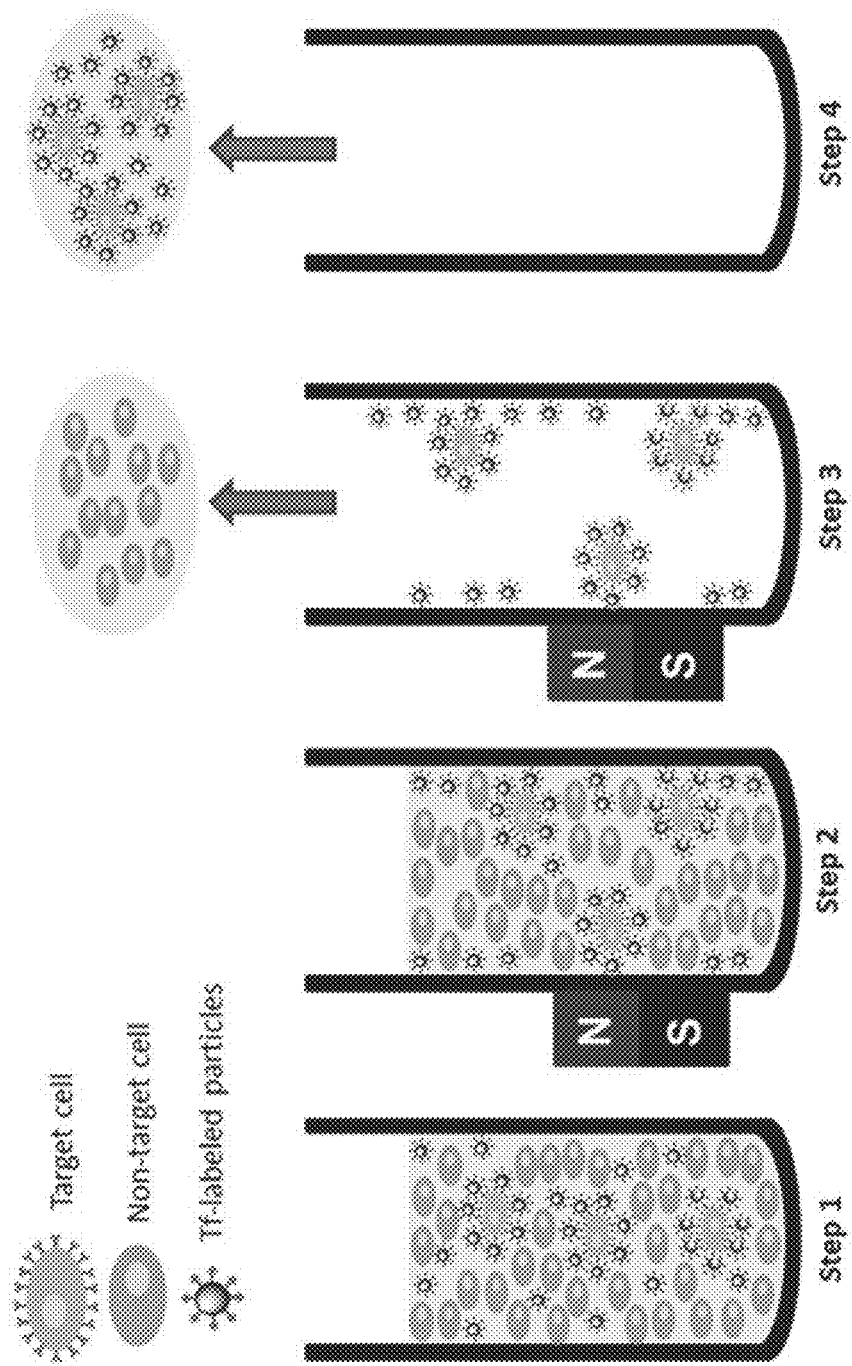
FIG. 8 illustrates a method of capturing target cells. Step 1: Tf-labeled particles bound to targeted cells, which were spiked into medium containing a larger amount of non-targeted cells. Step 2: Magnetic separation. Step 3: Removal of supernatant as well as nontarget cells. Step 4: Re-suspending and obtaining target cells.

Biomarker-targeted application is a major focus of nanomaterial development with a wide variety of targeting ligands, including small-molecules, peptides, proteins, antibodies and their fragments, polysaccharides, and aptamers, being used and explored. The conjugation reaction conditions for assembling ligands to the nanoparticle surface have to be as mild and biocompatible as possible to maintain the biological functions of targeting ligands. Sulfosuccinimidyl-4-(N-maleimidomethyl)cyclohexane-1-carboxylate (Sulfo-SMCC) was used to conjugate peptide cyclo-(RGDfC) (RGD) and holo-transferrin (human). See FIG. 7.

A small peptide RGD and a large protein transferrin (Tf), both frequently used to test nanoparticle targeting of overexpressed integrin or transferrin receptor (TfR), were used as the model ligands to demonstrate the robustness of the conjugations of different classes of targeting ligands to the PEG-b-AGE polymer coated IONP. The successful attachments of the targeting ligands to the PEG-b-AGE polymer coated IONP were first confirmed by the observed increase in hydrodynamic diameters and change of z-potentials of the nanoparticle after conjugations (Table 1).

PEG-b-AGE polymer coated IONPs with —NH$_2$ group functionalized have slightly positive surface potential due to the presence of —NH$_2$ groups. The surface charge of the nanoparticle became negative as the result of the neutralization of —NH$_2$ groups when ligands were covalently conjugated. The greater absolute values of z-potential for particle with 20 nm core size comparing to the one with 10 nm core can be ascribed as a higher number of targeting ligands conjugated on the larger particle which has more —NH$_2$ groups. This hypothesis was confirmed by the —NH$_2$ group quantification using ninhydrin. Since RGD is a small peptide that should not expand the hydrodynamic diameters significantly, the hydrodynamic diameters of the particles (with core diameters of both 10 nm and 20 nm) slightly increased after conjugation with RGD. On the other hand, the conjugation with a large protein, such as transferrin (80 kDa), led to a significant increase in the hydrodynamic diameter. The average number of transferrin molecules attached to each nanoparticle is 2.4 estimated by comparing the protein concentration to the IONP concentration of the Tf-IONP. Since RGD has an aspartic acid (asp) residue that contains one COOH group, the average number of conjugated RGD can be determined by quantifying the number of COOH groups. It was found that 456±60 and 1447±105 RGD peptides were conjugated to the IONPs with core diameters of 10 nm and 20 nm, respectively.

Reduced Non-Specific Cell Uptake of Nanoparticles and Improved Targeting

The innate immune system or the non-specific immune system, including monocytes, macrophages, dendritic cells, etc., is responsible for the immune response and cleaning out foreign materials from the body. Macrophages in particular play the key role in clearance of nanoparticles and reducing the long term toxicity, recognizing and then engulfing systemically administered nanoparticles. However, non-specific macrophage uptake of nanoparticles and ensuing migrations lead to shortened blood circulation and low level of delivery of nanoparticle probes to the targeted diseased region as well as off-target background signals.

RAW264.7 macrophage, a frequently used mouse macrophage cell line, was selected to examine the capability of PEG-b-AGE coated IONPs to avoid non-specific cellular uptake before and after conjugations with targeting ligands. Before the conjugation with targeting ligands, the PEG-b-AGE polymer coated IONP showed no uptake by macrophages after incubating with RAW264.7 cells for three hours at the Fe concentration of 0.2 mg mL$^{-1}$. After the conjugation with ligands RGD or Tf, it was found that the RGD-conjugated PEG-b-AGE polymer coated IONPs (RGD-IONP) still showed no uptake by macrophages, even though the surface property of the particle had been altered due to the introduction of the targeting ligands. The macrophage cells exhibited a very low level uptake of Tf-conjugated PEG-b-AGE polymer coated IONP (Tf-IONP), which can be attributed to a low level expression of TfR in RAW264.7 macrophage. As a control, the amphiphilic polymer coated SHP-10 exhibited significant uptake by macrophages even at the Fe concentration of 0.025 mg mL$^{-1}$. The improved targeting capabilities as the result of the antibiofouling property of the conjugated RGD or Tf conjugated PEG-b-AGE polymer coated IONPs were examined in vitro using different cancer cell lines with different cell marker expressions.

For RGD-IONP, MDA-MB-231 breast cancer cells and U87MG glioblastoma cells were selected as the positive control for testing RGD targeting the tumor integrin because both cells have high expression of the integrin $\alpha_v\beta_3$. MCF-7 breast cancer cells with low expression of the integrin $\alpha_v\beta_3$ were used as the negative control. Before the conjugation of RGD targeting ligand, no PEG-b-AGE coated IONP uptake was observed for all three different cancer cell lines. After conjugating with RGD targeting ligands, only cells with high expression of the integrin $\alpha_v\beta_3$, i.e., U87MG and MDA-MB-231, exhibited the uptake of RGD-IONPs, but not with the negative control MCF-7 breast cancer cells (FIG. 4H). In comparison, an intensive uptake of amphiphilic copolymer coated SHP-10 by U87MG, MDA-MB-231, and MCF-7 cells was observed even without the conjugation of RGD targeting ligand, which suggested the attenuation of targeting efficiency as a result of the off-target effect and background interference from non-specific normal cell uptake. The cell uptake results and the comparison clearly demonstrated the excellent targeting specificity of the RGD conjugated PEG-b-AGE polymer coated IONP attributed to its anti-biofouling property to avoid non-specific cell uptake.

For testing Tf-IONP, D556 and Daoy medulloblastoma cells with high expression of TfR were selected for the experiments. Lung cancer A549 cells with very low levels of TfR expression were used as a control. No uptake of PEG-b-AGE coated IONPs was observed for all three different cancer cells. However, when using Tf-IONPs, only the D556 and Daoy cancer cells with high expression of the TfR exhibited the uptake of the Tf-IONPs, but no uptake of Tf-IONP could be observed for the control of A549 lung cancer cells. In contrast, intensive uptake of the non-targeted SHP by D556, Daoy and A549 cells was observed, making it difficult to differentiate the different levels of TfR in different cells. Taken together, the results clearly indicated the excellent and improved targeting specificity and efficiency of the ligand conjugated PEG-b-AGE polymer coated IONP by minimizing non-specific cell uptake with anti-biofouling properties.

Reduced Protein Adsorption on PEG-b-AGE Polymer Coated IONPs

In soluble media such as blood, serum proteins can nonspecifically adsorb onto the surface of nanoparticles and form stable protein corona very rapidly upon contacting nanoparticles. To test whether PEG-b-AGE polymer can reduce the formation of protein corona around the coated IONPs, the nanoparticles were incubated with the protein containing media for one hour to allow the adsorption of proteins and formation of the corona. Given the better efficiency of magnetic separation used in this experiment, the particles with 20 nm core diameter were used. After the surface protein corona was washed off by KCl solution, the protein concentrations in the wash-off solution were measured using the bicinchoninic acid (BCA) protein assay. As shown in FIG. 3A, for the PEG-b-AGE polymer coated IONP (with a core diameter of 20 nm), the protein concentrations of the wash-off solutions were 47 mg mL$^{-1}$ for particle in FBS, and 97 mg mL$^{-1}$ in human plasma. In comparison, iron oxide nanoparticles coated with conventional amphiphilic triblock copolymer (SHP with a core diameter of 20 nm), which has 2012±162 —COOH groups on the surface, had protein concentrations in the washed-off solution of 623 mg mL$^{-1}$ in FBS, and 792 mg mL$^{-1}$ in human plasma. The significantly reduced level of proteins adsorbed on the surface of PEG-b-AGE polymer coated IONP clearly indicate efficiently reducing the non-specific protein adsorption onto the nanoparticle surface, suggesting the excellent anti-biofouling property of the developed PEG-b-AGE coating polymer.

Figure 3B:
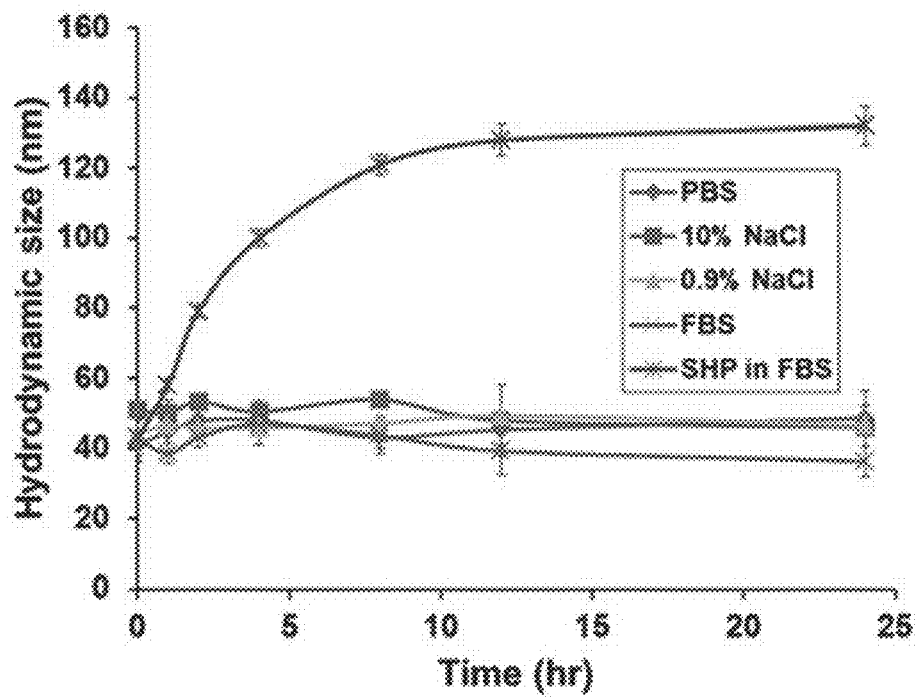
FIG. 3B shows data on the stability of PEG-b-AGE polymer coated IONP (with a core diameter of 20 nm) in PBS, 10% (w/v) NaCl aqueous solution, 0.9% NaCl aqueous solution, and 100% FBS, compared with amphiphilic triblock polymer coated SHP-20 in 10% FBS at the Fe concentration of 0.1 mg mL$^{-1}$.

Since the formation of corona can change the size, shape and surface charge of nanoparticles the anti-biofouling property of PEG-b-AGE polymer coated IONPs was examined by measuring the size stability in protein containing medium. The hydrodynamic size of PEG-b-AGE polymer coated IONP (with a core diameter of 20 nm) demonstrated remarkable stability against the protein adsorption in 100% FBS within 24 hours with only slight change of the hydrodynamic size, as shown in FIG. 3B, suggesting that the presence of the proteins in the media did not change the surface properties of the PEG-b-AGE polymer coated IONPs significantly. In contrast, the hydrodynamic size of SHP-20 exhibited substantial increase in hydrodynamic size from 45 nm to 130 nm over a period of 24 hour incubation when exposed to only 10% FBS. These results are in great accordance with the results of the surface protein corona measurement, suggesting the anti-biofouling properties of the PEG-b-AGE polymer coated IONPs.

PEG-b-AGE polymer coated IONP also exhibited good stability in PBS and 10% NaCl solutions (shown in FIG. 3B), which provided high surface charge and ionic strength that may lead to particle aggregation. The PEG-b-AGE polymer coated IONP showed little change in hydrodynamic size in both PBS and 10% NaCl solution. When 0.9% NaCl solution was used to mimic the physiological ionic strength, PEG-b-AGE polymer coated IONP demonstrated good stability in 0.9% NaCl solution as well.

In Vitro Cell Cytotoxicity Analysis

In order to apply the PEG-b-AGE polymer coated IONP to biomedical purposes, a cytotoxicity evaluation of the particle was carried out. RAW264.7 macrophage cells, U87MG glioblastoma cells, MDA-MB-231 breast cancer cells, MCF-7 breast cancer cells, Hela cells, D556 medulloblastoma cells, Daoy medulloblastoma cells, and A549 lung cancer cells were selected to incubate with PEG-b-AGE coated IONP (with a core diameter of 10 nm) with Fe concentration ranging from 0.500 mg mL$^{-1}$ to 0.008 mg mL$^{-1}$ for 24 hours. Afterwards, cell viability was estimated using the MTT conversion test. Even when the PEG-b-AGE polymer coated IONP was added at exceedingly high concentrations at 0.500 mg mL$^{-1}$, the cell survival rates still reached 83% for macrophage cells. The PEG-b-AGE polymer coated IONP at lower concentrations did not exhibit statistically significant cytotoxicity. For cancer cells, cell viabilities started to decrease when treated with PEG-b-AGE polymer coated IONPs at higher concentrations (0.250 and 0.500 mg mL$^{-1}$). The patterns of reduced cell viabilities were also observed when treating these cells with PEG-b-AGE polymer coated IONPs for much longer time (3 days).

Target Specific MRI Contrast Change and Reduction of Off-Target Background

Figure 4A:
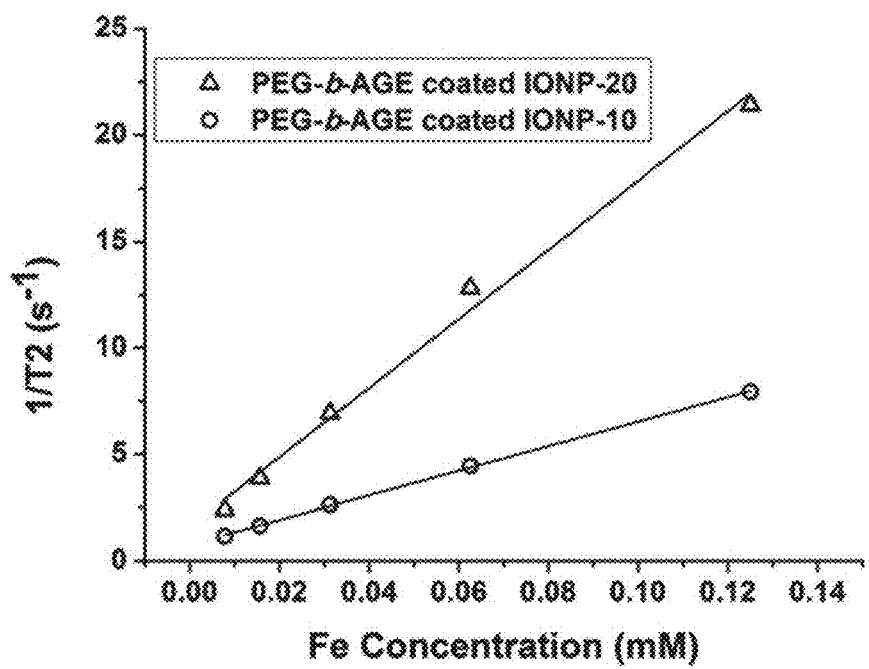
FIG. 4A shows data on transverse relaxation rates (R2 or 1/T2, s$^{-1}$) of PEG-b-AGE coated IONPs (with core diameters of 10 and 20 nm) as a function of the Fe concentration (mM).
Figure 4B:
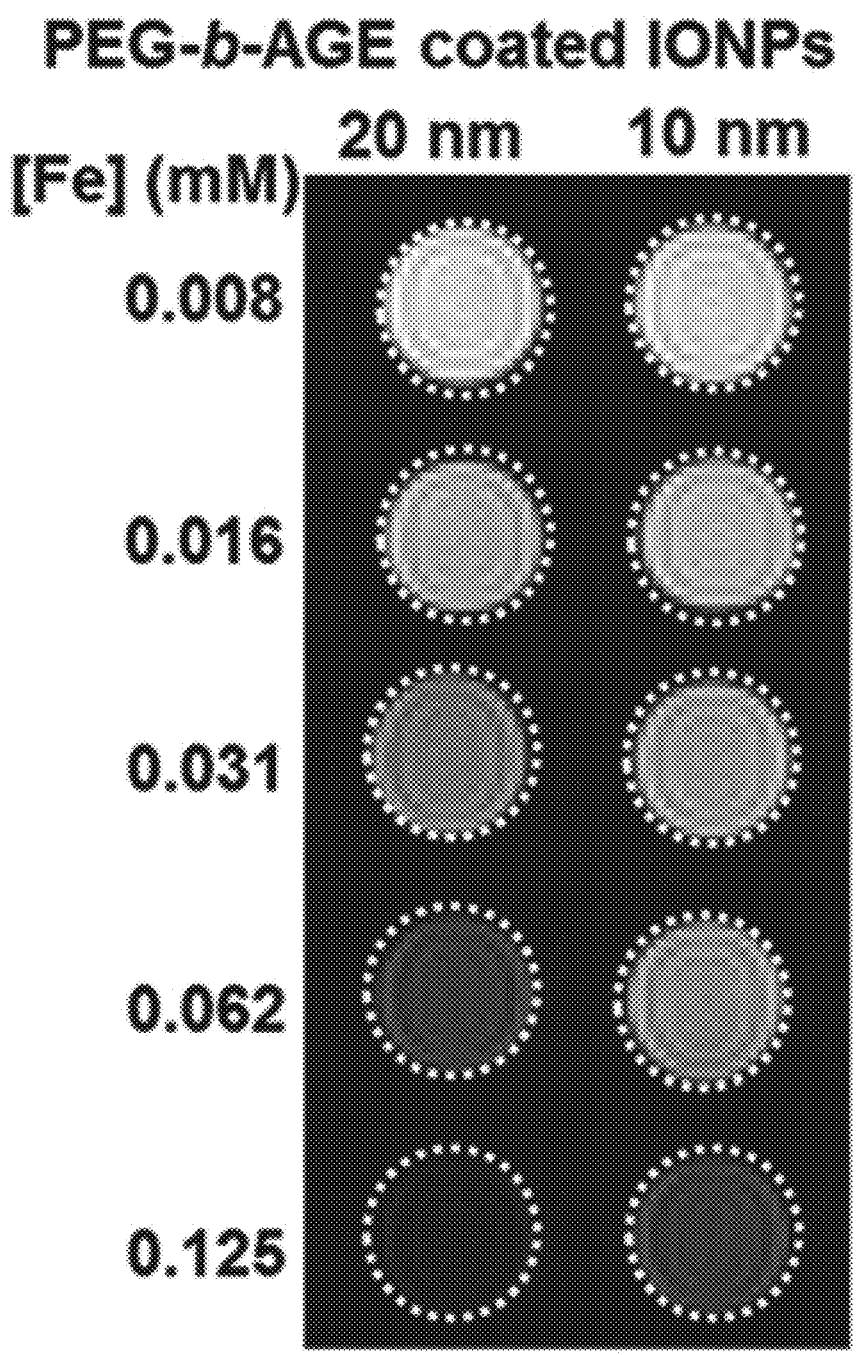
FIG. 4B shows T$^2$-weighted spin echo MR images of PEG-b-AGE coated IONPs (with core diameters of 10 and 20 nm) at different concentrations.

IONPs are mostly used as superb T2-weighted MRI contrast agents, typically causing signal drops in MRI by sharply shortening the transverse relaxation time T2 and dephasing the signal with induced susceptibility. To assess the potential of the PEG-b-AGE polymer coated IONP being an imaging probe, the transverse relaxation time T2 was determined by fitting the MRI signal intensities at different echo times (n=20) with an exponential function. The transverse relaxivity (r2) was calculated from the slopes of the linear correlation between the relaxation rates (1/T2) and iron concentrations. A typical hypointense contrast from the PEG-b-AGE polymer coated IONP was observed in T2-weighted spin echo images (FIG. 4B), and the transverse relaxivities of the IONPs were calculated to be 57.6 mM$^{-1}$ s$^{-1}$ and 162.6 mM$^{-1}$ s$^{-1}$ respectively for nanoparticles with core diameters of 10 nm and 20 nm (FIG. 4A).

Figure 5A:
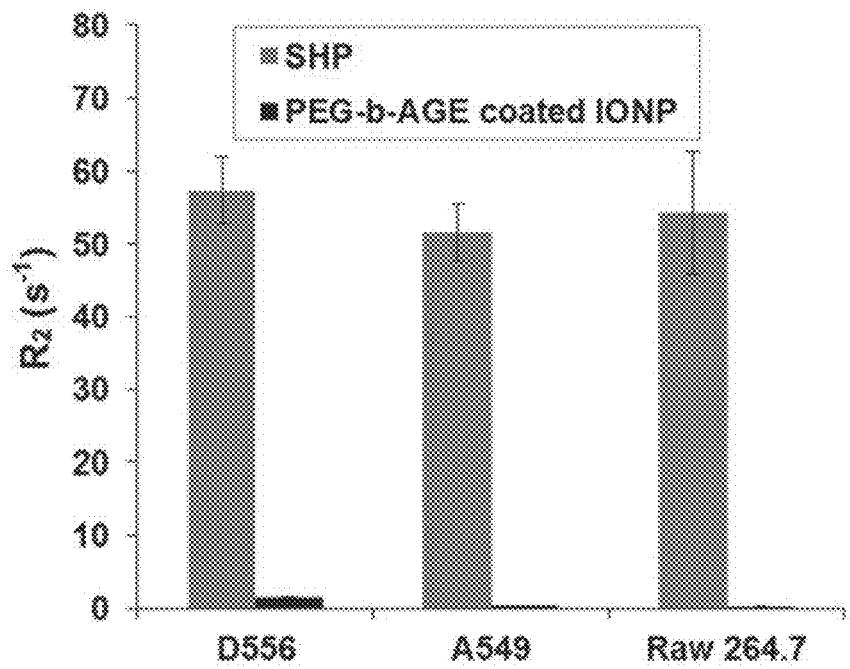
FIG. 5A shows data on R2 values indicating improved targeting by the antibiofouling property of PEG-b-AGE coated IONP. R2 values of cell phantoms containing D556 medulloblastoma cells, A549 lung cancer cells, and RAW264.7 macrophage cells treated with SHP and PEG-b-AGE coated IONP.

To examine whether reducing non-specific uptake and offtarget background by anti-biofouling PEG-b-AGE polymer can improve specificity of MRI contrast change that is directly related to the targeting cell biomarker, cell phantoms containing D556 medulloblastoma cells, A549 lung cancer cells, and RAW264.7 macrophage cells, were prepared and treated with Tf conjugated IONPs with or without anti-biofouling PEG-b-AGE coating. Because 20 nm particle has greater transverse relaxation rate (R2) than 10 nm particle (i.e. better contrast under same condition), the PEG-b-AGE coated IONP with a core diameter of 20 nm and SHP-20 were used for the phantom preparation. R2 (or 1/T2) relaxometry mapping of these cell phantoms showed substantial increase of R2 values in cells (e.g., D556, A549 and RAW264.7 cells) treated with SHP-20 but no significant change of R2 value in cells treated with PEG-b-AGE polymer coated IONPs, with the exception of a slight increase of the R2 values in PEG-b-AGE polymer coated IONPs with D556 medulloblastoma cancer cells (FIG. 5A). Since R2 value is directly proportional to the amount of IONP taken up by cells (i.e. the higher the R2 value, the more IONP taken up by cells), the R2 (or 1/T2) relaxometry results from cell phantom (in FIG. 5A) suggest a significant reduction of off-target background with PEG-b-AGE polymer coated IONPs comparing to conventional polymer coated SHP-20, attributed to the anti-biofouling effect of the PEG-b-AGE coating polymer.

Figure 5B:
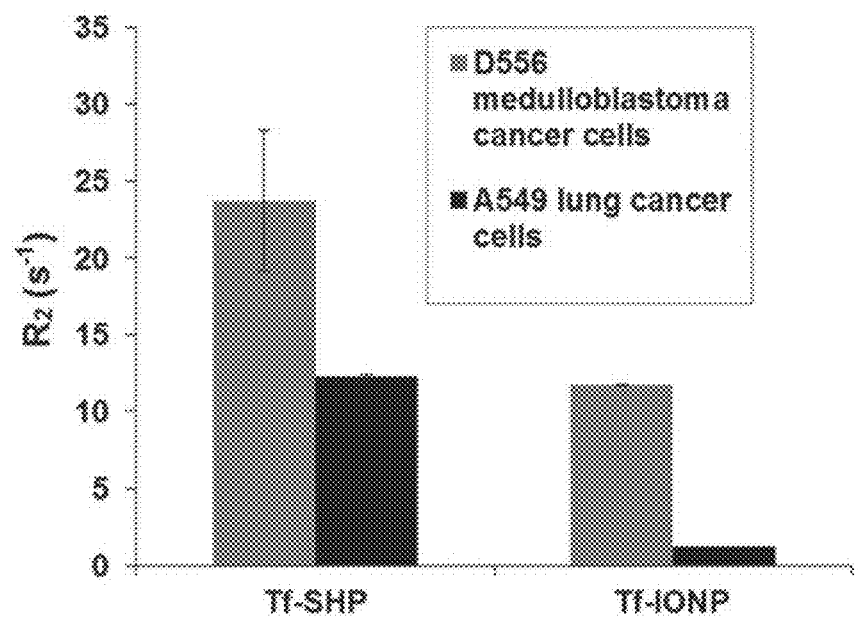
FIG. 5B shows data on D556 medulloblastoma cells and A549 lung cancer cells treated with Tf-SHP, and Tf-IONP.

With transferrin as the targeting ligand, Both Tf-SHP and PEG-b-AGE polymer coated Tf-IONP showed expected increase of contrast or "darkening" in T2-weighted MRI (increased R2 value) in D556 cells compared to non-targeted SHP-20 and IONPs as well as the control A549 cells (FIG. 5B), due to a higher level of transferrin receptor expression in D556 cells. However, The control A549 cells treated with TfR targeted SHP-20 showed substantially lower signal level comparing to A549 cells treated with PEG-b-AGE polymer coated Tf-IONP, suggesting that anti-biofouling effect from PEG-b-AGE polymer coated Tf-IONP led to the reduction of non-specific uptake of targeted IONPs by the cells not presenting targeted biomarkers, therefore, attenuated off-targeted background signal (FIG. 5B). Taking together, receptor targeted PEG-b-AGE polymer coated IONPs can improve targeted specific delivery and image contrast by not only maintaining ligand—target interactions without interference of "protein corona" or other surface adhesion of biomolecules, but also reducing the off-target background signals led by non-specific cell uptake of targeted IONPs. The reduction of the background from the non-specific off targeting signal is important, as this improvement allows for considering using targeted nanoparticle imaging probes (e.g., MRI, optical imaging or nuclear imaging) to determine and even quantify the levels of targeted biomarkers. The imaging probes thus not only can detect the overexpressed disease biomarkers, but also provide the quantitative capability to monitor disease progression or treatment responses. Furthermore, the reduction of off-target uptake of nanoparticles in background may also benefit the nanoparticle based drug delivery by improving the targeted delivery and minimizing the toxicity due to the normal tissue uptake.

Specificity of Cell Binding by Tf-Conjugated Nanoparticles

Medulloblastoma D556 cells with over-expressed TfR, lung cancer A549 cells with very low TfR expression and mouse macrophage Raw264.7 cells were cultured in EMEM, DMEM and RPMI1640, respectively. Media was supplemented with 10% (v/v) FBS, 1% (v/v) streptomycin and penicillin and cells were grown in a 5% $CO_2$ atmosphere at 37° C. $2 \times 10^4$ cells were seeded into 8-well chamber slides (Lab-Tek™ II, Thomas Scientific) and grown for 24 hours before experiments were performed. Culture media was aspirated and replaced by particle-containing media and the cells were cultured for three hours at 37° C. followed by Prussian blue staining to verify the uptake of the iron oxide nanoparticles (IONPs). To validate the effect of the PEG-b-AGE coated IONPs on reducing non-specific cellular uptake, PEG-b-AGE coated IONPs or SHP were incubated with Raw264.7 macrophage cells at the Fe concentration of 0.2 or 0.025 mg/mL, respectively. Transferrin conjugated PEG-b-AGE coated IONPs (Tf-IONP) or SHP (Tf-SHP) at the Fe concentration of 0.2 mg/mL were also used to treat D556 or A549 cells to examine the specific binding and internalization of Tf-conjugated particles with non-targeted PEG-b-AGE coated IONPs or SHP as control. Binding specificity was further tested and confirmed by the blocking assay by incubating D556 medulloblastoma cells with 400 molar excess of Tf for 30 minutes to block TfR prior to the addition of FITC-Tf-IONPs or FITC-Tf-SHP.

Influence of Protein Adsorption on Receptor Targeting

To examine the interference of non-specific protein adsorption on the particle surface with targeting of nanoparticles and the anti-biofouling effect, FITC-Tf-IONP and FITC-Tf-SHP ([Fe]=1 mg/mL) were pre-treated with 50% (v/v) FBS in PBS at room temperature for one hour incubation. The FBS treated nanoparticles were separated magnetically from the solution by applying an external magnet for two hours, followed by re-suspending the collected materials in PBS. The separation-re-suspension was repeated three times. The protein concentration was determined using the bicinchoninic acid (BCA) protein assay. The protein corona concentration was defined by the difference of protein concentration (μg protein/mg IONP) between FBS treated and non-treated IONPs. Both FBS pre-treated and non-treated FITC-Tf-IONP and FITC-Tf-SHP were then incubated with D556 medulloblastoma and A549 lung cancer cells in culture media with the Fe concentration of 0.2 mg/mL at 37° C. for three hours. Afterwards the supernatant was removed, and the cells were rinsed with PBS three times. For the purpose of fluorescent imaging, $2 \times 10^4$ cells (either D556 medulloblastoma or A549 lung cancer cells) were seeded into an 8-well chamber slide and grown for 24 hours before incubating with nanoparticles. After incubation, the cells were fixed with 4% paraformaldehyde for 20 minutes, followed by rinsing with deionized water three times. The slide was then mounted with prolong gold anti-fade mounting reagent containing DAPI. To evaluate the effect of protein corona on cell targeting, fluorescence signals of FITC from the FBS pre-treated and non-treated nanoparticles taken up by cells were measured. $5 \times 10^3$ D556 medulloblastoma or A549 lung cancer cells were seeded into a 96-well plate. The cells were grown at 37° C. for 24 hours before incubating with nanoparticles. Afterwards, the cells were lysed for the measurement of fluorescence signal from FITC on a plate reader to assess whether the protein adsorption on the IONP surface might affect the binding of the IONPs to the cells. The signal intensity was averaged from six wells.

Specificity of Cell Capture

To investigate the effect of anti-biofouling property on the specificity of capturing targeted cells, Tf-IONPs or Tf-SHP was cultured with a mixture of $1 \times 10^5$ TfR over-expressed D556 cells pre-stained with CMFDA (green fluorescence) and $1 \times 10^5$ A549 cells with low expression level of TfR as "background" in a final volume of 1.0 mL and Fe concentration of 0.2 mg/mL. After incubating at 37° C. for two hours and separating magnetically for 45 minutes, the supernatant was removed. The captured cells were re-suspended in PBS and examined by flow cytometry (FCM, BD FACSCanto™ II RUO Special Order System, BD Biosciences) or smeared onto a slide and fixed with 4% paraformaldehyde in PBS, followed by DAPI staining (blue fluorescence) for fluorescent imaging using microscope (BX41, Olympus).

To further examine the specificity of isolating target cells using anti-biofouling magnetic IONPs, the separation of target cells in the presence of an excess amount of unwanted cells was investigated using FITC-Tf-IONP and FITC-Tf-SHP. Briefly, 100 CMFDA pre-stained D556 medulloblastoma cells with over-expressed TfR were spiked into culture medium containing $1 \times 10^5$ A549 lung cancer cells that have very low level of TfR expression. FITC-Tf-IONP or FITC-Tf-SHP was added to the cell mixture at the final volume of 1.0 mL and Fe concentration of 0.2 mg/mL. The solutions were cultured at 37° C. for two hours followed by the application of an external magnet for 45 minutes at room temperature to allow cells labeled with IONPs to form a pellet. The supernatant was removed and the captured cells were re-suspended with PBS, transferred to poly-L-lysine (PLL)-coated chamber and cultured at 37° C. for two hours allowing the cells to attach to the chamber. The cells were washed three times with PBS and then fixed with 4% paraformaldehyde in PBS for 20 minutes before DAPI staining for nucleus. Fluorescent imaging for green fluorescence from FITC labeled IONPs and blue fluorescence from DAPI stained nucleus was used to identify target D556 medulloblastoma cells or non-target A549 lung cancer cells.

Sensitivity of Cell Capture with Magnetic Nanoparticles

Currently most immunomagnetic separation procedures are performed using commercially available micron-sized magnetic particles or beads. The major advantage of using micron-sized beads is their strong magnetism, thus rendering them to be easily separated using very low-field benchtop permanent magnets. This process is robust and efficient when extracting large amount of wanted cells from a small amount of unwanted cells. However, for the separation of a small number of targeted cells (as in most clinical settings), nanoparticles may have significant advantages over using micron-sized particles or beads, including (1) more surface area for conjugating targeting ligands, thus more interactions with cell surface markers; (2) greater amount of nanoparticles bound or even internalized by the targeted cells than micron-sized beads, thus collectively, to gain sufficient magnetism for magnetic separation, and (3) maintenance of cell integrity and viability with less magnetic force-induced stress on the captured cells when additional molecular characterizations of the captured cells needed to be carried out, which typically involve in culture and expanding a few or even single captured cells.

To validate whether magnetic IONPs are more sensitive than micron-sized particles in cell separation, the efficiencies of capturing TfR over-expressed D556 medulloblastoma cells using both PEG-b-AGE coated IONP and Dynabeads® conjugated with Tf were evaluated. $2 \times 10^4$ Medulloblastoma D556 cells were stained with DiI (red fluorescence) according to manufacturer's manual, and then seeded into a 12-well plate and cultured for two days. The cells were then incubated either with FITC-Tf-IONPs at the Fe concentration of 0.2 mg/mL or $2 \times 10^6$ Tf-Beads in 1 mL of PBS for two hours at 37° C. Afterwards, cells were washed with PBS three times, detached from the plate, and transferred into a tube for magnetic separation. An external magnet was applied to the tube for 45 minutes at room temperature to allow the magnetic particle labeled D556 cells to attach to the tube. The supernatant was separated from the attached cells, which were then re-suspended with PBS. Both supernatant and cell re-suspension were transferred to poly-L-lysine (PLL)-coated chamber and cultured for two hours at 37° C. for the cells to attach to the chamber. The cells were then fixed with 4% paraformaldehyde for 20 minutes before DAPI staining for nucleus. The average number of beads bound to the cells was calculated based on measuring 20 cells randomly selected from the microscopic field of view.

$$\text{Capture efficiency} = N_{capture}/(N_{capture} + N_{super}) \qquad \text{Eq. 1}$$

The cell capture efficiency was defined by Equation 1 shown above, where $N_{capture}$ and $N_{super}$ are the average numbers of cell counted from six different microscopic views (10× magnification) of magnetically captured cells and the cells in supernatant respectively.

To assess the sensitivity of cell capture, the number of cells captured and separated by an external magnet after FITC-Tf-IONP or Dynabeads® (M-450 epoxy) conjugated with FITC-Tf (FITC-Tf-Bead) was estimated (incubated with $2 \times 10^4$ D556 medulloblastoma cells for two hours at 37° C., respectively). Counting the number of cells observed based on strong fluorescence from FITC and DAPI, 95.5±1.4% of the D556 medulloblastoma cells were captured by FITC-Tf-IONP, indicating sufficient magnetism from nanoparticles for magnetic separation. Weak fluorescence from FITC was observed for the cells left in the supernatant.

Figure 9:
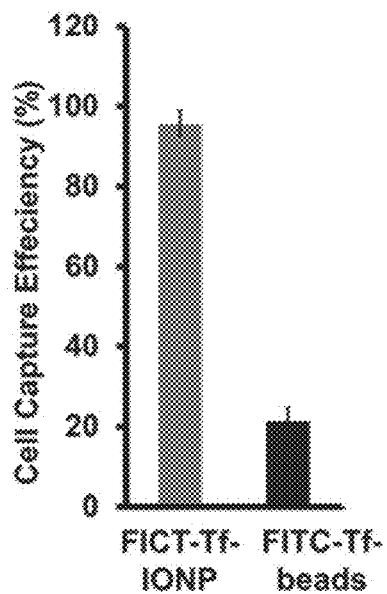
FIG. 9 shows efficiency data from fluorescent images of D556 medulloblastoma cells captured capture using FITC-Tf-IONP and FITC-Tf-beads.

In comparison, only 21.3±1.7% of D556 cells could be captured using FITC-Tf-beads (FIG. 9A) using the experimental conditions of this study, compared with 95.5% using nanoparticles. The low capture sensitivity of micron-sized beads can be explained by the higher steric hindrance and less ligand-to-cell interactions, given that Dynabeads® and cells are of the same order of magnitude in size. The larger the bead, the harder it binds to cells through ligand-to-target interactions.

For the cells treated with FITC-Tf-bead, only 5.45±3.19 (n=20) beads can attach onto each captured cell even when the initial ratio of beads to cell was 100:1. In contrast, a large number of Tf-IONP nanoparticles could be targeted and bound to a single cell, thus conferring the ease of magnetic isolation. The D556 cells separated by Tf-IONP were further examined by TEM to validate the large number of IONP accumulations inside cells.

Specificity of Receptor Mediated Cell Separation

As major effort and emphasis are placed on improving the CTC detection sensitivity, the specificity (i.e. rate of capturing unwanted cells), although practically important, is often overlooked. Inadequate specificity not only contributes to making the process of cell separation labor-intensive and time-consuming, but it also, in turn, leads to a high false-positive rate and reduces the sensitivity of CTC detection owing to the low signal-to-noise ratio. For instance, separation of CTCs by the CellSearch® technology, the only FDA-approved CTC detection product available commercially, yields only 0.01-0.1% in purity (CTCs/captured cells).

Figure 10:
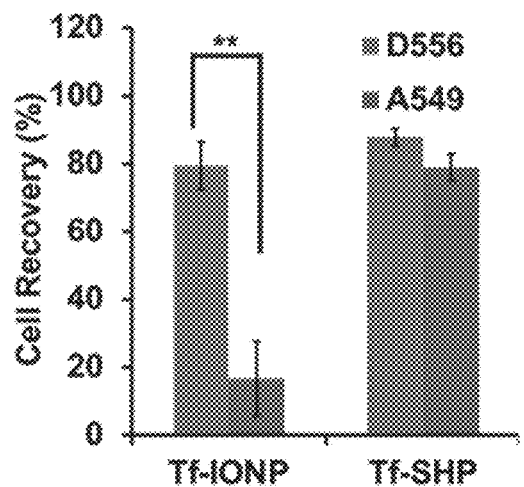
FIG. 10 shows capture rate data for D556 medulloblastoma cells and A549 lung cancer cells using Tf-IONP or Tf-SHP.

To test whether adopting anti-biofouling coating strategy may improve the specificity of isolating targeted cells, Tf-IONP were used to capture targeted cells from a mixture containing an equal number ($1 \times 10^5$) of non-target cells. Tf-SHP was used for comparison. From the mixture of same number of D556 medulloblastoma cells (pre-stained by CMFDA) and A549 lung cancer cells, Tf-IONP successfully captured 79.0±4.0% (n=3) of D556 medulloblastoma cells but only 16.7±4.4% (n=3) of A549 lung cancer cells. The specificity of targeted cell capture by Tf-IONP was found to be 83%. Meanwhile, Tf-SHP also captured 87.1±5.2% (n=3) of the D556 medulloblastoma cells from the cell mixture. However, 79.3±4.2% (n=3) of non-targeted A549 lung cancer cells were also captured by Tf-SHP, resulting in a specificity of 53% (FIG. 10).

Cells separated by Tf-IONP contained much less non-targeted A549 lung cancer cells than those captured by Tf-SHP. The flow cytometry (FCM) evaluation of the captured cells was in great agreement with the cell enumeration. The similar signal intensity from D556 medulloblastoma cells (peaks centered at $10^4$) separated by Tf-IONP and Tf-SHP, as well as the much lower signal from A549 lung cancer cells (peaks centered at $10^3$) captured by Tf-IONP than Tf-SHP, are indicative of the higher proportion of targeted cells (D556 cells with green fluorescence from CMFDA) among all captured one isolated using Tf-IONP.

Figure 11:
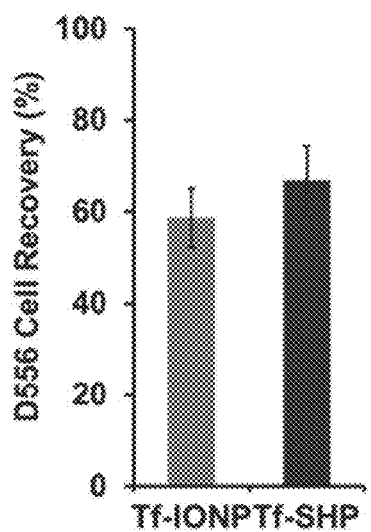
FIG. 11 shows data on the numerations of captured D556 medulloblastoma cells from mixture of pre-stained D556 cells with 1000-fold A549 lung cancer cells.

To further evaluate the potential of PEG-b-AGE coated IONP in rare CTCs detection, the separation of 100 CMFDA pre-stained D556 cells from $1 \times 10^5$ A549 cells using Tf-IONP was investigated with Tf-SHP as control. It was found that 58.7±6.4% (n=3) and 62.7±7.6% (n=3) of targeted D556 medulloblastoma cells were separated using both Tf-IONP and Tf-SHP respectively (FIG. 11) with no statistically significant difference (p>0.05), suggesting that both Tf-IONP and Tf-SHP (with the same size of core and magnetic properties) possessed similarly high sensitivity in isolating cells as low as 100 cells/mL. However, cells captured by Tf-SHP contained a great amount of non-targeted A549 lung cancer cells, leading to a lower specificity rate, while Tf-IONP mainly captured D556 medulloblastoma cells. The privileged specificity from anti-biofouling PEG-b-AGE coated IONP enabled an excellent signal-to-noise ratio without sacrificing the sensitivity of cell capture.

The invention claimed is:

1. A polymer having the following formula:

[chemical structure: H₂N−(−O−)ₚ−X−(−)ₘ−Si(OR)₃₋ₙR'ₙ]

wherein p is 1 to 10,000;
m is 1 to 22;
X is —CH(OH)CH₂OCH₂CH₂CH₂S—;
n=0, 1, 2;
R is an alkyl group, and
R' is alkyl group.

2. A polymer having the following formula:

[chemical structure with H₂N−(−O−)ₙ− group, ether linkages, OH, S, and Si(OR)₃]

wherein R is alkyl and n is 1 to 10,000 or derivative thereof.

3. A substrate coated with a polymer made by the process of mixing a substrate and the polymer under conditions such that a siloxane-coated substrate is formed, wherein the polymer has the following formula:

[chemical structure: H₂N−(−O−)ₚ−X−(−)ₘ−Si(OR)₃₋ₙR'ₙ]

wherein p is 1 to 10,000;
m is 1 to 22;
X is —CH(OH)CH₂OCH₂CH₂CH₂S—;
n=0, 1, 2;
R is an alkyl group, and
R' is alkyl group.

4. A particle coated with a polymer made by the process of mixing a particle and the polymer under conditions such that a siloxane-coated particle is formed wherein the polymer has the following formula:

[chemical structure: H₂N−(−O−)ₚ−X−(−)ₘ−Si(OR)₃₋ₙR'ₙ]

wherein p is 1 to 10,000;
m is 1 to 22;
X is —CH(OH)CH₂OCH₂CH₂CH₂S—;
n=0, 1, 2;
R is an alkyl group, and
R' is alkyl group.

5. The particle of claim 4, wherein the particle comprises a metal or metal oxide core.

6. The particle of claim 5, wherein the particle has of an average core diameter of between 3 nm to 1000 nm.

7. The particle of claim 4, wherein the terminal amine group is further conjugated to a targeting moiety.

8. The particle of claim 7, wherein the targeting moiety is an antibody, antibody fragment, affibody, or peptide based ligand.

9. A particle having a siloxane coating of the formula:

[chemical structure with H₂N−(−O−)ₙ− group, ether linkages, OH, S, and Si(OR)₃]

wherein n is 1 to 10,000 and R is a siloxane connecting point to the surface of the particle.

10. A particle having a siloxane coating of the following formula:

[chemical structure: W−Z−NH−(−O−)ₙ− group with ether linkages, OH, S, and Si(OR)₃]

wherein W is a targeting moiety, Z is a linking group, n is 1 to 10,000 and R is a siloxane connecting point to the surface of the particle.

11. A method of separating cells comprising
a) providing a contained area comprising nanoparticles, wherein the nanoparticles have a siloxane coating of the following formula:

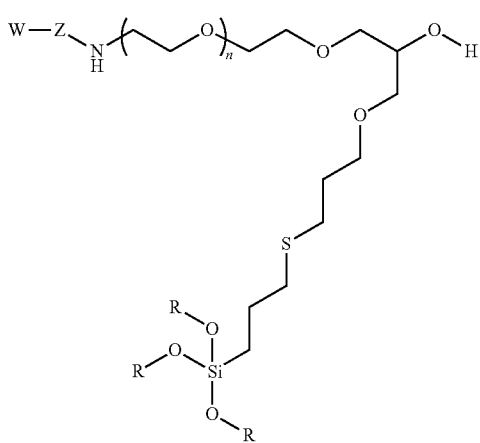

wherein W is a targeting moiety, Z is a linking group, n is 1 to 10,000, and R is a siloxane connecting point to the surface of the nanoparticles;

b) mixing the nanoparticles with a mixture of cells comprising target cells and non-target cells, wherein target cells comprise a moiety that the targeting group binds under conditions such that the nanoparticles bind with target cells;

c) exposing the contained area to a magnetic field; and d) moving the non-target cells such that the target cells are restrained to the magnetic field thereby separating non-target cells from target cells.

12. A method detecting the presence of a cell in a confined area of a subject comprising a) administering a composition comprising nanoparticles under conditions such that the nanoparticles bind to target cells, wherein nanoparticles have a siloxane coating the following formula:

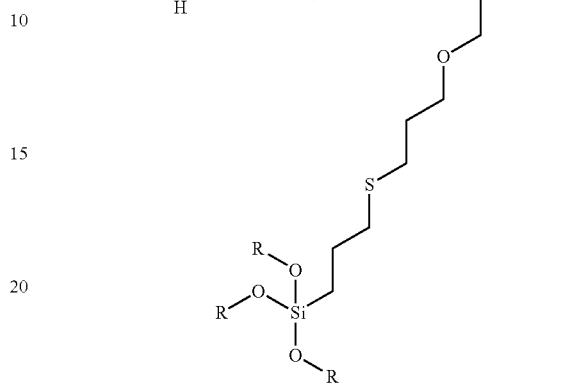

wherein W is a targeting moiety, Z is a linking group, n is 1 to 10,000, and R is a siloxane connecting point to the surface of the nanoparticles;

b) exposing the confined area to magnetic field; and c) detecting the presence of the nanoparticles in the confined area.

* * * * *